(12) United States Patent
Steinman et al.

(10) Patent No.: US 7,579,328 B2
(45) Date of Patent: Aug. 25, 2009

(54) DNA VACCINATION FOR TREATMENT OF MULTIPLE SCLEROSIS AND INSULIN-DEPENDENT DIABETES MELLITUS

(75) Inventors: Lawrence Steinman, Palo Alto, CA (US); Pedro Ruiz, Menlo Park, CA (US); Hideki Garren, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 11/289,226

(22) Filed: Nov. 28, 2005

(65) Prior Publication Data
US 2006/0084623 A1    Apr. 20, 2006

Related U.S. Application Data

(63) Continuation of application No. 09/947,770, filed on Sep. 5, 2001, now Pat. No. 7,030,098, which is a continuation-in-part of application No. PCT/US00/06233, filed on Mar. 10, 2000, which is a continuation-in-part of application No. 09/267,590, filed on Mar. 12, 1999, now abandoned.

(51) Int. Cl.
*A01N 43/04* (2006.01)
*C12N 15/00* (2006.01)

(52) U.S. Cl. ..................... 514/44; 435/320.1
(58) Field of Classification Search .............. 514/44; 435/320.1
See application file for complete search history.

(56) References Cited

U.S. PATENT DOCUMENTS 5,939,400 A    8/1999    Steinman et al.

FOREIGN PATENT DOCUMENTS

| WO | WO 86/01540 |   | 3/1986 |
| WO | WO 94/23737 | A | 10/1994 |
| WO | WO 97/45144 |   | 12/1997 |
| WO | WO 97 45144 |   | 12/1997 |
| WO | WO 97/45144 | A | 12/1997 |
| WO | WO 97 46253 |   | 12/1997 |
| WO | WO 97/46253 | A | 12/1997 |
| WO | WO 00/78360 |   | 12/2000 |

OTHER PUBLICATIONS

Concalves M, A concise peer into the bqackground, initial thoughts, and practices of human gene therapy, 2005, BioEssays, vol. 27, pp. 506-517.*
Parekh-Olmedo H, Gene therapy progress and prospects: targeted gene rapair, 2005, Gene Therapy, vol. 12, pp. 639-646.*
Verma IM, Gene Therapy: Twenty-first century medicine, 2005, Annu. Rev. Biochem. vol. 74, pp. 711-738.*
Liu M, Immunization of non-human primates with DNA vaccines, 1997, vol. 15, pp. 909-912.*
Elliott E, Immune tolerance mediated by recombinant proteolipid protein prevents experimental autoimmune encephalomyelitis, J. of Neuroimmunology, 1997, vol. 79, pp. 1-11.*
Karpus W, Inhibition of relapsing experimental autoimmune enchephalomyelitis in SJL mice by feeding the immunodominant PLP139-151 peptide, 1996, J. of Neuroscience Res., vol. 45, pp. 410-423.*
Harrison L, The prospect of vaccination to prevent type I diabetes, 2005, Human Vaccines, vol. 1, pp. 143-150.*
Ichinose et al., Recent advancement of understanding pathogenesis of type I diabetes and potential relevance to diabetic nephrothapy, 2007, Am J Nephrology, vol. 27, pp. 554-564.*
Di Marzio et al., Macroangiopathay in adults and children with diabetes: from molecular mechanisms to vascular damage, 2006, Horm Metab Res., vol. 38, pp. 691-705.*
Concalves M, A concise peer into the background, initial thoughts, and practices of human gene therapy, 2005, BioEssays, vol. 27, pp. 506-517.*
Parekh-Olmedo H, Gene therapy progress and prospects: targeted gene repair, 2005, Gene Therapy, vol. 12, pp. 639-646.*
Verma IM, Gene Therapy: Twenty-first century medicine, 2005, Annu. Rev. Biochem. vol. 74, pp. 711-738.*
Yang et al., Lessons on autoimmune diabetes from animal models, 2006, Clinical Sciences, vol. 110, pp. 627-639.*
Sasaki et al., Adjuvant formulations and delivery systems for DNA vaccines, 2003, Methods, vol. 31, pp. 243-254.*
Editorial, Guns, genes and spleen: a coming of age for rational vaccine design, 2003, Methods, vol. 31, pp. 183-192.*
Donnolly et al., 2005, J. Immunology, vol. 175, pp. 633-639.*
Toyoda et al., 1998, Bioessays, vol. 20(9), pp. 750-757.*
Coon et al., Jul. 1999, JCI, vol. 104(2), pp. 189-194.*
Krieg et al., 1998, PNAS, vol. 95, pp. 12631-12636.*
Krieg et al., 1999, J. Gene Med., vol. 1, pp. 56-63.*
Krieg et al., 1998, Trends in Microbiology, vol. 6(1), pp. 23-27.*
Ristori et al. (2000)Myelin Basic protein intramolecular spreading without disease progression in a patient with multiple sclerosis. J. of Neuroimmunology. 110:240-243.*
Ellmerich et al. (2005) High Incidence of Spontaneous Disease in an HLA-DR15 and TCR Transgenic Multiple Sclerosis Model. J. Immunol. 174:1938-1946.*
Elkman L. (2005) Voluntary Suspension of Tysabri Marketing. Letter, pp. 1-2.*
Sobel et al, Neurochem Res. 19:915-921, 1994.*
Klinman et al . The Journal of Immunology 158:3635-3639, 1997.*
Baker et al (Gene Therapy 10:844-853, 2003.*

(Continued)

*Primary Examiner*—Peter Paras, Jr.
*Assistant Examiner*—David Montanari
(74) *Attorney, Agent, or Firm*—Townsend and Townsend and Crew LLP

(57) ABSTRACT

A pro-inflammatory T cell response is specifically suppressed by the injection into a recipient of DNA encoding an autoantigen associated with autoimmune disease. The recipient may be further treating by co-vaccination with a DNA encoding a Th2 cytokine, particularly encoding IL4. In response to the vaccination, the proliferation of autoantigen-reactive T cells and the secretion of Th1 cytokines, including IL-2, IFN-γ and IL-15, are reduced.

10 Claims, 7 Drawing Sheets

OTHER PUBLICATIONS

Nowicka J et al., "Protective Effect of Naked DNA Immunization in Experimental Autoimmune Encephalitis.", *Journal of Neuroimmunology*, Sep. 1, 1998, p. 102, vol. 90(1).

Chow YH et al., "Development of Th1 and Th2 Populations and the Nature of Immune Responses to Hepatitis B Virus DNA Vaccines Can Be Modulated by Codelivery of Various Cytokine Genes", *Journal of Immunology*, Feb. 1, 1998, pp. 1320-1329, vol. 160(3).

Ruiz PJ et al., Suppressive Immunization with DNA Encoding a Self-Peptide Prevents Autoimmune Disease: Modulation of T Cell Costimulation, *Journal of Immunology*, Mar. 15, 1999, pp. 3336-3341, vol. 162(6).

Garren Hideki et al., "Combination of Gene Delivery and DNA Vaccination to Protect From and Reverse Th1 Autoiimune Disease Via Deviation to the Th2 Pathway", *Immunity*, Jul. 2001, pp. 15-22, vol. 15(1).

Kolodka, Tadeusz M., et al., "Gene therapy for diabetes mellitus in rats by hepatic expression of insulin", *Proceedings of the National Academy of Sciences USA*, Apr. 1995, pp. 3293-3297, vol. 92, National Academy of Science, Washington, D.C., United States.

Urbanek-Ruiz, Irene, et al., "Immunization with DNA Encoding an Immunodominant Peptide of Insulin Prevents Diabetes in NOD Mice", *Clinical Immunology*, Aug. 2001, pp. 164-171, vol. 100 No. 2, Academic Press, United States.

Anderton et al., European Journal of Immunology, Apr. 1998, vol. 28:1251-1261.

Barnett et al., Journal of Neuroimmunology, vol. 64:163-173.

Bebo et al., Journal of Neuroscience Research, vol. 45:680-689.

Cohen, et al., Hosp. Practice, May 1997, pp. 169-177.

Davis, et al., Human Mol. Genetics, 1993, V.11, pp. 1847-1851.

Davis, et al., Vaccine, 1994 V. 12, No. 16, pp. 1503-1509.

Falo, et al., Nature Medicine, V . 4, No. 11, Nov. 1998, pp. 1239-1240.

Greer, et al., J. of Immunology, V. 149, Aug. 1992, pp. 783-788.

Kerlero de Rosbo, et al., J. of Autoimmunity, 1998, V. 11, pp. 287-299.

King, et al., Nature Medicine, V. 4, No. 11, Nov. 1998, pp. 1281-1286.

Krieg, et al., Trends in Microbiology, V. 6, No. 1, Jan. 1998, pp. 23-27.

Leadbetter, et al., J. of Immunology, Mar. 1998, 161, pp. 504-512.

Ledley, FD., Pharmaceutical Research, vol. 13:1595-1613.

Mor, et al., Am. Assoc. of Immunologists, 1995, V. 155, pp. 2039-2046.

Nicholson, et al., Proc. Natl. Acad. Sci., V. 94, Aug. 1997, pp. 9279-9284.

Offner, et al., J. of Immunology, 1998, V. 161, pp. 2178-2186.

Oksenberg, et al., Curr. Opinion in Immunology, 1990, V. 2, pp. 619-621.

Oksenberg, et al., Nature, V. 362, Mar. 1993, pp. 68-70.

Pardoll, et al., Immunity, V. 3, Aug. 1995, pp. 165-169.

Rawshaw et al., Immunology and Cell Biology, vol. 75:409-413.

Sato et al., Science, vol. 273-352-354.

Syrengelas, et al., Nature Medicine, V. 2(9), Sep. 1996, pp. 1038-1041.

Tang, et al., Nature, V. 356, Mar. 1992, pp. 152-154.

Tsunoda et al., Journal of Neuropathology and Experimental Neurology, vol. 57(8):758-767.

Ulmer, et al., Current Opinion in Immunology, 1996, vol. 8, pp. 531-536.

Ulmer, et al., Science, V. 259, Mar. 1993, pp. 1745-1749.

Waisman, et al., Nature Medicine, V. 2(8), Aug. 1996, pp. 899-905.

Xu, et al., Immunology, V. 84, 1995, pp. 173-176.

Diehl, Hans-Josef, et al.; "Individual exons encode the integral membrane domains of human myelin proteolipid protein", *Proc. Natl. Acad. Sci.*; 1986, pp. 9807-9811, vol. 83.

Kamholz, John, et al.; "Identification of three forms of human myelin basic protein by cDNA cloning", *Proc. Natl. Acad. Sci.*; 1986; pp. 4962-4966; vol. 83.

Pham-Dinh, Danielle, et al.; "Characterization and expression of the cDNA coding for the human myelin/oligodendrocyte glycoprotein", *J. Neurochemistry*; 1994; pp. 2353-2356, vol. 63.

Hilton, Adrienne A., et al.; "Characterization of cDNA and genomic clones encoding human myelin oligodendrocyte glycoprotein", *J. Neurochemistry*; 1995; pp. 309-318, vol. 65.

Sato, Shuzo, et al.; "cDNA cloning and amino acid sequence for human myelin-associated glycoprotein"; *Biochemical and Biophysical Research Communications*; Sep. 29, 1989; pp. 1473-1480; vol. 163, No. 3.

Spagnol; G., et al.; "Molecular cloning of human myelin-associated glycoprotein", *Journal of Neuroscience Research.*; 1989; pp. 137-142; vol. 24.

Trotter, John L., et al.; "T cell recognition of myelin proteolipid protein and myelin proteolipid protein peptides in the peripheral blood of multiple sclerosis and control subjects", *Journal of Neuroimmunology*; 1998; pp. 172-178; vol. 84.

Meinl, Edgar, et al.; "Myelin basic protein-specific T lymphocyte repertoire in multiple sclerosis—complexity of the response and dominance of nested epitopes due to recruitment of multiple T cell clones"; *J. Clin. Invest.*; 1993, pp. 2633-2643; vol. 92.

Martin, Roland, et al.; "Fine Specificity and HLA restrictions of myelin basic protein-specific cytotoxic T cell lines from multiple sclerosis patients and healthy individuals"; *The Journal of Immunology*; 1990; pp. 540-548; vol. 145.

Wallstrom, Erik, et al.; "Increased reactivity to myelin oligodendrocyte peptides and epitope mapping in HLA DR2(15)+ multiple sclerosis", *Eur. J. Immunol.*; 1998; pp. 3329-3335, vol. 28.

Tuohy, Vincent K., et al.; "The epitope spreading cascade during progression of experimental autoimmune encephalomyelitis and multiple sclerosis"; *Immunological Reviews*; 1998; pp. 93-100; vol. 164.

Takacs, Katalin, et al.; "The case against epitope spread in experimental allergic encephalomyelitis", *Immunological Review*; 1998; pp. 101-110; vol. 164.

Takacs, Katalin, et al.; "Relapsing and remitting experimental allergic encephalomyelitis: a focused response to the encephalitogenic peptide rather than epitope spread"; *Eur. J. Immunol.*; 1997; pp. 2927-2934; vol. 27.

Tuohy, Vincent, et al.; "Spontaneous regression of primary autoreactivity during chronic progression of experimental autoimmune encephalomyelitis and multiple sclerosis"; *J. Exp. Med.*; Apr. 5, 1999; pp. 1033-1042; vol. 189, No. 7.

Smilek, Dawn E., et al.; "A single amino acid change in a myelin basic protein peptide confers the capacity to prevent rather than induce experimental autoimmune encephalomyelitis", *Proc. Natl. Acad. Sci.*; Nov. 1991; pp. 9633-9637, vol. 88.

Gaur, Amitabh, et al.; "Amelioration of relapsing experimental autoimmune encephalomyelitis with altered myelin basic protein peptides involves different cellular mechanisms", *Journal of Neuroimmunology*; 1997; pp. 149-158, vol. 74.

Kuchroo, Vijay K., et al.; "A single TCR Antagonist peptide inhibits experimental allergic encephalomyelitis mediated by a diverse T cell repertoire"; *The Journal of Immunology*; 1994; pp. 3326-3336; vol. 153.

Warren, K. G., et al.; "Tolerance induction to myelin basic protein by intravenous synthetic peptides containing epitope $P_{85}VVHFFKNIVTP_{96}$ in chronic progressive multiple sclerosis"; *Journal of Neurological Sciences*; 1997; pp. 31-38; vol. 152.

Crowe, Paul D., et al.; "Differential signaling and hierarchical response thresholds induced by an immunodominant peptide of myelin basic protein and an altered peptide ligand in human T cells"; *Human Immunology*; 1998; pp. 679-689; vol. 59.

Aharoni, Rina, et al.; "Copolymer 1 induces T cells of the T helper type 2 that crossreact with myelin basic protein and suppress experimental autoimmune encephalomyelitis"; *Proc. Natl. Acad. Sci.*; Sep. 1997; pp. 10821-10826; vol. 94.

Coon et al., (1999), "DNA immunization to prevent autoimmune diabetes", *J. Clin. Invest.*, 104(2):189-94.

Garren et al., (2001), "Combination of gene delivery and DNA vaccination to protect from and reverse Th1 autoimmune disease via deviation to the Th2 pathway", *Immunity*, 15:15-22.

IFNB_MS_Study_Group (1995), "Interferon beta-1b in the treatment of multiple sclerosis: final outcome of the randomized controlled trial", *Neurology*, 45:1277-85.

Lisak, et al., (1983), "Effect of treatment with Copolymer 1 (Cop-1) on the in vivo and in vitro manifestations of experimental allergic encephalomyelitis (EAE)", *J. Neurol. Sci.* 62:281-93.

Mikol, et al. (1990), "Structure and chromosomal location of the gene for the oligodendrocyte-myelin glycoprotein", *J. Cell Biol.*, 111(6 pt 1):2673-2679.

Sela, and Teitelbaum, (2001), "Glatiramer acetate in the treatment of multiple sclerosis", *Expert Opin. Pharmacother.*, 2:1149-1165.

Steinman, (1990), "The use of monoclonal antibodies for treatment of autoimmune disease", *J. Clin. Immunol.*, 10(6):30S-38S; discussion 38S-39S.

Urbanek-Ruiz, et al., (2001), "Immunization with DNA encoding an immunodominant peptide of insulin prevents diabetes in NOD mice", *Clin. Immunol.*, 100:164-171.

Van Oosten, et al. (1997), "Treatment of multiple sclerosis with the monoclonal anti-CD4 antibody cM-T412: results of a randomized, double-blind, placebo-controlled, MR- monitored phase II trial", *Neurology*, 49:3551-357.

Wiest-Ladenburger, et al., (1998), "DNA vaccination with glutamic acid decarboxylase (GAD) generates a strong humoral immune response in BALB/c, C57BL/6, and in diabetes-prone NOD mice", *Horm. Metab. Res.*, 30(10):605-609.

Yasuda et al., "Interferon beta modulates experimental autoimmune encephalomyelitis by altering the pattern of cytokine secretion", *Immunol. Invest.* 28:115-126.

Brocke,, S., Gijbels, K., Allegretta, M., Ferber, I., Piercy, C., Blankenstein, T., Martin, R., Utz, U., Karin, N., Mitchell, D., et al. (1996). Treatment of experimental encephalomyelitis with a peptide analogue of myelin basic protein, Nature 379, 343-6.

Bu DF et al Two human glutamate decarboxylases, 65-kDa GAD and 67-kDa GAD, are each encoded by a single gene. Proc Natl Acad Sci USA 89(6):2115-2119, 1992.

Jacobs, Lawrence et al., Extended observations on MS patients treated with IM interfereon-β 1a (Avonex™): implications for modern MS trials and therapeutics Presented in part at Pathogenic and Regulatory Cells in Demyelinating Diseases, Rome, Italy, Sep. 12-15, 1999., Journal of Neuroimmunology, (2000), vol. 107, pp. 167-173.

Johnson, K. P., Brooks, B. R., Cohen, J. A., Ford, C. C., Goldstein, J., Lisak, R. P., Myers, L. W., Panitch, H. S., Rose, J. W., and Schiffer, R. B. (1995). Copolymer 1 reduces relapse rate and improves disability in relapsing- remitting multiple sclerosis: results of a phase III multicenter, double-blind placebo-controlled trial. The Copolymer 1 Multiple Sclerosis Study Group, Neurology 45, 1268-76.

Kamholz J et al. Identification of three forms of human myelin basic protein by cDNA cloning. Proc Natl Acad Sci USA 83:4962-6. 1986.

Kappos, L., Comi, G., Panitch, H., Oger, J., Antel, J., Conlon, P., and Sleinman, L. (2000). Induction of a non-encephalitogenic type 2 T helper-cell autoimmune response in multiple sclerosis after administration of an altered peptide ligand in a placebo-controlled, randomized phase II trial. The Altered Peptide Ligand in Relapsing MS Study Group, Nat Med 6, 1176-82.

Karin, N., Mitchell, D. J., Brocke, S., Ling, N., and Steinman, L. (1994). Reversal of experimental autoimmune encephalomyelitis by a soluble peptide variant of a myelin basic protein epitope: T cell receptor antagonism and reduction of interferon gamma and tumor necrosis factor alpha production, J Exp Med 180, 2227-37.

Liblau RS, Singer SM, McDevitt HO. Th1 and Th2 CD4+ T cells in the pathogenesis of organ-specific autoimmune diseases. Immunol Today Jan. 1995;16(1):34-8.

Lobell, A. et al., Vaccination with DNA Encoding an Immunodominant Myelin Basic Protein Peptide Targeted to Fc of Immunoglobulin G Suppresses Experimental Autoimmune Encephalomyelitis, J. Exp. Med. (1998), vol. 187-No. 9, pp. 1543-1548.

Lobell, A. et al., Presence of CpG DNA and the Local Cytokine Milieu Determine the Efficacy of Suppressive DNA Vaccination in Experimental Autoimmune Encephalomyelitis, The Journal of Immunology, (1999), vol. 163, pp. 4754-4762.

Miller, A., Lider, O., Abramsky, O., and Weiner, H. L. (1994). Orally administered myelin basic protein in neonates primes for immune responses and enhances experimental autoimmune encephalomyelitis in adult animals, Eur J Immunol 24, 1026-32.

Simons R. et al. Human myelin DM-20 proteolipid protein deletion defined by cDNA sequence. Biochem Biophys Res Commun 146(2):666-671, 1987.

Spagnol G, et al. Molecular cloning of human myelin-associated glycoprotine. J Neurosci Res 24:137-42. 1989.

Teitelbaum D, Fridkis-Hareli M, Amon R, Sela M. (1995) Copolymer 1 Inhibits chronic relapsing experimental allergic encephalomyelitis induced by proteolipid protein (PLP) peptides in mice and Interferes with PLP-specific T cell responses. J Neuroimmunology 64, 209-217.

Tubridy, N., Behan, P. O., Capildeo, R., Chaudhuri, A., Forbes, R., Hawkins, C. P., Hughes, R. A., Palace, J., Sharrack, B., Swingler, R., et al. (1999). The effect of anti-alpha4 integrin antibody on brain lesion activity in MS. The UK Antegren Study Group, Neurology 53, 466-72.

Tuohy VK, Yu M, Yin L, Mathisen PM, Johnson JM, Kawczak JA. (2000) Modulation of the IL-10/IL-12 cytokine circuit by interferon-beta inhibits the development of epitope spreading and disease progression in murine autoimmune encephalomyelitis. J Neuroimmunol 111,55-63.

Weiner, H. L., Friedman, A., Miller, A., Khoury, S. J., al-Sabbagh, A., Santos, L., Sayegh, M., Nussenblatt, R. B., Trentham, D. E., and Hafler, D. A. (1994). Oral tolerance: immunologic mechanisms and treatment of animal and human organ-specific autoimmune diseases by oral administration of autoantigens. Annu Rev Immunol 12, 809-37.

Yednock, T. A., Cannon, C., Fritz, L. C., Sanchez-Madrid, F., Steinman, L., and Karin, N. (1992). Prevention of experimental autoimmune encephalomyelitis by antibodies against alpha 4 beta 1 integrin, Nature 356. 63-6.

Yu M, Nishiyama A, Trapp BD, Tuohy VK. (1996) Interferon-beta inhibits progression of relapsing-remitting experimental autoimmune encephalomyelitis. J. Neuroimmunology 64,91-100.

Nowicka et al., "Protective effect of naked DNA immunization in experimental autoimmune encephalitis." Journal of Neuroimmunology, vol. 90, No. 1, (Sep. 1, 1998), p. 102, abstract 582 XP001068792 ISSN: 0165-5728.

Ruiz et al., "Suppressive Immunization with DNA Encoding a Self-Peptide Prevents Autoimmune Disease: Modulation of T Cell Costimulation", Journal of Immunology, vol. 162, No. 6, (Mar. 15, 1999). p. 3336-3341, XP002196043.

* cited by examiner peptide concentration (mg/ml)

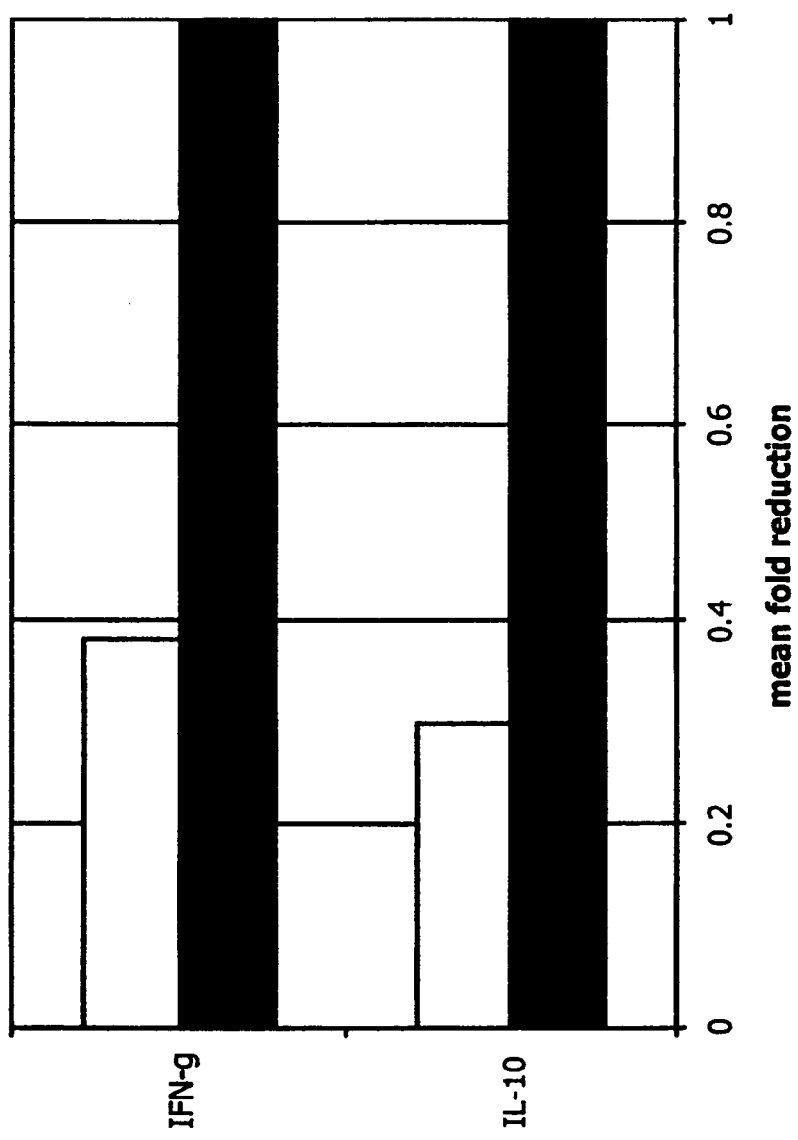

SEQUENCE LISTING

```
<160> NUMBER OF SEQ ID NOS: 34

<210> SEQ ID NO 1
<211> LENGTH: 2777
<212> TYPE: DNA
<213> ORGANISM: Homo sapiens
<220> FEATURE:
<221> NAME/KEY: CDS
<222> LOCATION: (119)...(952)

<400> SEQUENCE: 1
gaattcggga aaagaccgaa gaaggaggct ggagagacca ggatccttcc agctgaacaa      60
agtcagccac aaagcagact agccagccgg ctacaattgg agtcagagtc ccaaagac      118 atg ggc ttg tta gag tgc tgt gca aga tgt ctg gta ggg gcc ccc ttt      166
Met Gly Leu Leu Glu Cys Cys Ala Arg Cys Leu Val Gly Ala Pro Phe
 1               5                  10                  15 gct tcc ctg gtg gcc act gga ttg tgt ttt ggg gtg gca ctg ttc          214
Ala Ser Leu Val Ala Thr Gly Leu Cys Phe Phe Gly Val Ala Leu Phe
             20                  25                  30 tgt ggc tgt gga cat gaa gcc ctc act ggc aca gaa aag cta att gag      262
Cys Gly Cys Gly His Glu Ala Leu Thr Gly Thr Glu Lys Leu Ile Glu
         35                  40                  45 acc tat ttc tcc aaa aac tac caa gac tat gag tat ctc atc aat gtg      310
Thr Tyr Phe Ser Lys Asn Tyr Gln Asp Tyr Glu Tyr Leu Ile Asn Val
     50                  55                  60 atc cat gcc ttc cag tat gtc atc tat gga act gcc tct ttc ttc ttc      358
Ile His Ala Phe Gln Tyr Val Ile Tyr Gly Thr Ala Ser Phe Phe Phe
```

-continued

```
            65                  70                  75                  80
ctt tat ggg gcc ctc ctg ctg gct gag ggc ttc tac acc acc ggc gca        406
Leu Tyr Gly Ala Leu Leu Ala Glu Gly Phe Tyr Thr Thr Gly Ala
                    85                  90                  95 gtc agg cag atc ttt ggc gac tac aag acc acc atc tgc ggc aag ggc        454
Val Arg Gln Ile Phe Gly Asp Tyr Lys Thr Thr Ile Cys Gly Lys Gly
                100                 105                 110 ctg agc gca acg gta aca ggg ggc cag aag ggg agg ggt tcc aga ggc        502
Leu Ser Ala Thr Val Thr Gly Gly Gln Lys Gly Arg Gly Ser Arg Gly
            115                 120                 125 caa cat caa gct cat tct ttg gag cgg gtg tgt act tgt ttg gga aaa        550
Gln His Gln Ala His Ser Leu Glu Arg Val Cys Thr Cys Leu Gly Lys
        130                 135                 140 tgg cta gga cat ccc gac aag ttt gtg ggc atc acc tat gcc ctg acc        598
Trp Leu Gly His Pro Asp Lys Phe Val Gly Ile Thr Tyr Ala Leu Thr
145                 150                 155                 160 gtt gtg tgg ctc ctg gtg ttt gcc tgc tct gct gtg cct gtg tac att        646
Val Val Trp Leu Leu Val Phe Ala Cys Ser Ala Val Pro Val Tyr Ile
                165                 170                 175 tac ttc aac acc tgg acc acc tgc cag tct att gcc ttc ccc agc aag        694
Tyr Phe Asn Thr Trp Thr Thr Cys Gln Ser Ile Ala Phe Pro Ser Lys
                180                 185                 190 acc tct gcc agt ata ggc agt ctc tgt gct gac gcc aga atg tat ggt        742
Thr Ser Ala Ser Ile Gly Ser Leu Cys Ala Asp Ala Arg Met Tyr Gly
            195                 200                 205 gtt ctc cca tgg aat gct ttc cct ggc aag gtt tgt ggc tcc aac ctt        790
Val Leu Pro Trp Asn Ala Phe Pro Gly Lys Val Cys Gly Ser Asn Leu
        210                 215                 220 ctg tcc atc tgc aaa aca gct gag ttc caa atg acc ttc cac ctg ttt        838
Leu Ser Ile Cys Lys Thr Ala Glu Phe Gln Met Thr Phe His Leu Phe
225                 230                 235                 240 att gct gca ttt gtg ggg gct gca gct aca ctg gtt tcc ctg ctc acc        886
Ile Ala Ala Phe Val Gly Ala Ala Ala Thr Leu Val Ser Leu Leu Thr
                245                 250                 255 ttc atg att gct gcc act tac aac ttt gcc gtc ctt aaa ctc atg ggc        934
Phe Met Ile Ala Ala Thr Tyr Asn Phe Ala Val Leu Lys Leu Met Gly
                260                 265                 270 cga ggc acc aag ttc tga tcccccgtag aaatcccccct ttctctaata              982
Arg Gly Thr Lys Phe *
            275 gcgaggctcc tctaaccaca cagcctacaa tgctgcgtct cccatcttaa ctctttgcct     1042 ttgccaccaa ctggccctct tcttacttga tgagtgtaac aagaaaggag agtcttgcag     1102 tgattaaggt ctctctttgg actctcccct cttatgtacc tcttttagtc attttgcttc     1162 atagctggtt cctgctagaa atgggaaatg cctaagaaga tgacttccca actcgaagtc     1222 acaaaggaat ggaggctcta attgaatttt caagcatctc ctgaggatca gaaagtaatt     1282 tcttctcaaa gggtacttcc actgatgaaa acaaagtgga aggaaagaag gtcaggtaca     1342 gagaaggaat gtctttggtc tcttgccat ctataggggc caaatatatt ctctttggtg      1402 tacaaaatgg aattcattct ggtctctcta ttaccactga agatagaaga aaaagaatg      1462 tcagaaaaac aataagagcg tttgcccaaa tctgcctatt gcagctggga aaggggggtc     1522 aaagcaagga tctttcaccc acagaaagag agcactgacc ccgatggcga tggactactg     1582 aagccctaac tcagccaacc ttacttacag cataagggag cgtagaatct gtgtagacga     1642 agggggcatc tggccttaca cctcgttagg gaagagaaac agggtgttgt cagcatcttc     1702 tcactcccctt ctccttgata acagctacca tgacaaccct gtggtttcca aggagctgag    1762
```

-continued

```
aatagaagga aactagctta catgagaaca gactggcctg aggagcagca gttcctggtg      1822
gctaatggtg taacctgaga tggccctctg gtagacacag gatagataac tctttggata     1882
gcatgtcttt ttttctgtta attagttgtg tactctggcc tctgtcatat cttcacaatg     1942
gtgctcattt catggggtat tatccattca gtcatcgtag gtgatttgaa ggtcttgatt     2002
tgttttagaa tgatgcacat ttcatgtatt ccagtttgtt tattacttat ttggggttgc     2062
atcagaaatg tctggagaat aattctttga ttatgactgt tttttaaact aggaaaattg     2122
gacattaagc atcacaaatg atattaaaaa ttggctagtt gaatctattg ggattttcta     2182
caagtattct gcctttgcag aaacagattt ggtgaatttg aatctcaatt tgagtaatct     2242
gatcgttctt tctagctaat ggaaaatgat tttacttagc aatgttatct ggtgtgtta     2302 agagttaggt ttaacataaa ggttattttc tcctgatata gatcacataa cagaatgcac     2362
cagtcatcag ctattcagtt ggtaagcttc caggaaaaag gacaggcaga aagagtttga     2422
gacctgaata gctcccagat ttcagtcttt tcctgttttt gttaactttg ggttaaaaaa    2482
aaaaaaagtc tgattggttt taattgaagg aaagatttgt actacagttc ttttgttgta    2542
aagagttgtg ttgttctttt cccccaaagt ggtttcagca atatttaagg agatgtaaga    2602
gctttacaaa aagacacttg atacttgttt tcaaaccagt atacaagata agcttccagg    2662
ctgcatagaa ggaggagagg gaaaatgttt tgtaagaaac caatcaagat aaaggacagt    2722
gaagtaatcc gtaccttgtg ttttgttttg atttaataac ataacaaata accaa        2777
```

<210> SEQ ID NO 2
<211> LENGTH: 277
<212> TYPE: PRT
<213> ORGANISM: Homo sapiens

<400> SEQUENCE: 2

```
Met Gly Leu Leu Glu Cys Cys Ala Arg Cys Leu Val Gly Ala Pro Phe
 1               5                  10                  15

Ala Ser Leu Val Ala Thr Gly Leu Cys Phe Phe Gly Val Ala Leu Phe
                20                  25                  30

Cys Gly Cys Gly His Glu Ala Leu Thr Gly Thr Glu Lys Leu Ile Glu
            35                  40                  45

Thr Tyr Phe Ser Lys Asn Tyr Gln Asp Tyr Glu Tyr Leu Ile Asn Val
        50                  55                  60

Ile His Ala Phe Gln Tyr Val Ile Tyr Gly Thr Ala Ser Phe Phe Phe
 65                  70                  75                  80

Leu Tyr Gly Ala Leu Leu Leu Ala Glu Gly Phe Tyr Thr Thr Gly Ala
                85                  90                  95

Val Arg Gln Ile Phe Gly Asp Tyr Lys Thr Thr Ile Cys Gly Lys Gly
            100                 105                 110

Leu Ser Ala Thr Val Thr Gly Gly Gln Lys Gly Arg Gly Ser Arg Gly
        115                 120                 125

Gln His Gln Ala His Ser Leu Glu Arg Val Cys Thr Cys Leu Gly Lys
    130                 135                 140

Trp Leu Gly His Pro Asp Lys Phe Val Gly Ile Thr Tyr Ala Leu Thr
145                 150                 155                 160

Val Val Trp Leu Leu Val Phe Ala Cys Ser Ala Val Pro Val Tyr Ile
                165                 170                 175

Tyr Phe Asn Thr Trp Thr Thr Cys Gln Ser Ile Ala Phe Pro Ser Lys
            180                 185                 190
```

```
Thr Ser Ala Ser Ile Gly Ser Leu Cys Ala Asp Ala Arg Met Tyr Gly
        195                 200                 205

Val Leu Pro Trp Asn Ala Phe Pro Gly Lys Val Cys Gly Ser Asn Leu
        210                 215                 220

Leu Ser Ile Cys Lys Thr Ala Glu Phe Gln Met Thr Phe His Leu Phe
225                 230                 235                 240

Ile Ala Ala Phe Val Gly Ala Ala Ala Thr Leu Val Ser Leu Leu Thr
                245                 250                 255

Phe Met Ile Ala Ala Thr Tyr Asn Phe Ala Val Leu Lys Leu Met Gly
        260                 265                 270

Arg Gly Thr Lys Phe
        275

<210> SEQ ID NO 3
<211> LENGTH: 2139
<212> TYPE: DNA
<213> ORGANISM: Homo sapiens
<220> FEATURE:
<221> NAME/KEY: CDS
<222> LOCATION: (37)...(552)

<400> SEQUENCE: 3
gaaaacagtg cagccacctc cgagagcctg gatgtg atg gcg tca cag aag aga         54
                                        Met Ala Ser Gln Lys Arg
                                          1               5 ccc tcc cag agg cac gga tcc aag tac ctg gcc aca gca agt acc atg        102
Pro Ser Gln Arg His Gly Ser Lys Tyr Leu Ala Thr Ala Ser Thr Met
            10                  15                  20 gac cat gcc agg cat ggc ttc ctc cca agg cac aga gac acg ggc atc        150
Asp His Ala Arg His Gly Phe Leu Pro Arg His Arg Asp Thr Gly Ile
        25                  30                  35 ctt gac tcc atc ggg cgc ttc ttt ggc ggt gac agg ggt gcg cca aag        198
Leu Asp Ser Ile Gly Arg Phe Phe Gly Gly Asp Arg Gly Ala Pro Lys
    40                  45                  50 cgg ggc tct ggc aag gac tca cac cac ccg gca aga act gct cac tat        246
Arg Gly Ser Gly Lys Asp Ser His His Pro Ala Arg Thr Ala His Tyr
55                  60                  65                  70 ggc tcc ctg ccc cag aag tca cac ggc cgg acc caa gat gaa aac ccc        294
Gly Ser Leu Pro Gln Lys Ser His Gly Arg Thr Gln Asp Glu Asn Pro
                75                  80                  85 gta gtc cac ttc ttc aag aac att gtg acg cct cgc aca cca ccc ccg        342
Val Val His Phe Phe Lys Asn Ile Val Thr Pro Arg Thr Pro Pro Pro
            90                  95                 100 tcg cag gga aag ggg aga gga ctg tcc ctg agc aga ttt agc tgg ggg        390
Ser Gln Gly Lys Gly Arg Gly Leu Ser Leu Ser Arg Phe Ser Trp Gly
        105                 110                 115 gcc gaa ggc cag aga cca gga ttt ggc tac gga ggc aga gcg tcc gac        438
Ala Glu Gly Gln Arg Pro Gly Phe Gly Tyr Gly Gly Arg Ala Ser Asp
    120                 125                 130 tat aaa tcg gct cac aag gga ttc aag gga gtc gat gcc cag ggc acg        486
Tyr Lys Ser Ala His Lys Gly Phe Lys Gly Val Asp Ala Gln Gly Thr
135                 140                 145                 150 ctt tcc aaa att ttt aag ctg gga gga aga gat agt cgc tct gga tca        534
Leu Ser Lys Ile Phe Lys Leu Gly Gly Arg Asp Ser Arg Ser Gly Ser
                155                 160                 165 ccc atg gct aga cgc tga aaacccacct ggttccggaa tcctgtcctc               582
Pro Met Ala Arg Arg *
            170 agcttcttaa tataactgcc ttaaaacttt aatcccactt gccctgtta cctaattaga       642
```

-continued

```
gcagatgacc cctcccctaa tgcctgcgga gttgtgcacg tagtagggtc aggccacggc    702
agcctaccgg caatttccgg ccaacagtta aatgagaaca tgaaaacaga aaacggttaa    762
aactgtccct ttctgtgtga agatcacgtt ccttcccccg caatgtgccc ccagacgcac    822
gtgggtcttc agggggccag gtgcacagac gtccctccac gttcacccct ccacccttgg    882
actttctttt cgccgtggct cggcacccct gcgcttttgc tggtcactgc catggaggca    942
cacagctgca gagacagaga ggacgtgggc ggcagagagg actgttgaca tccaagcttc   1002
ctttgttttt ttttcctgtc cttctctcac ctcctaaagt agacttcatt tttcctaaca   1062
ggattagaca gtcaaggagt ggcttactac atgtgggagc ttttttggtat gtgacatgcg   1122
ggctgggcag ctgttagagt ccaacgtggg gcagcacaga gagggggcca cctccccagg   1182
ccgtggctgc ccacacaccc caattagctg aattcgcgtg tggcagaggg aggaaaagga   1242
ggcaaacgtg ggctgggcaa tggcctcaca taggaaacag ggtcttcctg gagatttggt   1302
gatggagatg tcaagcaggt ggcctctgga cgtcaccgtt gccctgcatg gtggccccag   1362
agcagcctct atgaacaacc tcgtttccaa accacagccc acagccggag agtccaggaa   1422
gacttgcgca ctcagagcag aagggtagga gtcctctaga cagcctcgca gccgcgccag   1482
tcgcccatag acactggctg tgaccgggcg tgctggcagc ggcagtgcac agtggccagc   1542
actaaccctc cctgagaaga taaccggctc attcacttcc tcccagaaga cgcgtggtag   1602
cgagtaggca caggcgtgca cctgctcccg aattactcac cgagacacac gggctgagca   1662
gacggcccct gtgatggaga caaagagctc ttctgaccat atccttctta cacccgctg    1722
gcatctcctt tcgcgcctcc ctccctaacc tactgaccca cctttttgatt ttagcgcacc   1782
tgtgattgat aggccttcca aagagtccca cgctggcatc accctccccg aggacggaga   1842
tgaggagtag tcagcgtgat gccaaaacgc gtcttcttaa tccaattcta attctgaatg   1902
tttcgtgtgg gcttaatacc atgtctatta atatatagcc tcgatgatga gagagttaca   1962
aagaacaaaa ctccagacac aaacctccaa atttttcagc agaagcactc tgcgtcgctg   2022
agctgaggtc ggctctgcga tccatacgtg gccgcaccca cacagcacgt gctgtgacga   2082
tggctgaacg gaaagtgtac actgttcctg aatattgaaa taaaacaata aacttttt     2139
```

<210> SEQ ID NO 4
<211> LENGTH: 171
<212> TYPE: PRT
<213> ORGANISM: Homo sapiens

<400> SEQUENCE: 4

```
Met Ala Ser Gln Lys Arg Pro Ser Gln Arg His Gly Ser Lys Tyr Leu
 1               5                  10                  15

Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Phe Gly Gly
        35                  40                  45

Asp Arg Gly Ala Pro Lys Arg Gly Ser Gly Lys Asp Ser His His Pro
    50                  55                  60

Ala Arg Thr Ala His Tyr Gly Ser Leu Pro Gln Lys Ser His Gly Arg
65                  70                  75                  80

Thr Gln Asp Glu Asn Pro Val Val His Phe Phe Lys Asn Ile Val Thr
                85                  90                  95

Pro Arg Thr Pro Pro Pro Ser Gln Gly Lys Gly Arg Gly Leu Ser Leu
            100                 105                 110
```

```
Ser Arg Phe Ser Trp Gly Ala Glu Gly Gln Arg Pro Gly Phe Gly Tyr
        115                 120                 125
Gly Gly Arg Ala Ser Asp Tyr Lys Ser Ala His Lys Gly Phe Lys Gly
    130                 135                 140
Val Asp Ala Gln Gly Thr Leu Ser Lys Ile Phe Lys Leu Gly Gly Arg
145                 150                 155                 160
Asp Ser Arg Ser Gly Ser Pro Met Ala Arg Arg
                165                 170
```

<210> SEQ ID NO 5
<211> LENGTH: 13
<212> TYPE: PRT
<213> ORGANISM: Artificial Sequence
<220> FEATURE:
<223> OTHER INFORMATION: PLP139-151

<400> SEQUENCE: 5

```
His Ser Leu Gly Lys Trp Leu Gly His Pro Asp Lys Phe
1               5                   10
```

<210> SEQ ID NO 6
<211> LENGTH: 13
<212> TYPE: PRT
<213> ORGANISM: Artificial Sequence
<220> FEATURE:
<223> OTHER INFORMATION: PLP139-151 L144/R147

<400> SEQUENCE: 6

```
His Ser Leu Gly Lys Leu Leu Gly Arg Pro Asp Lys Phe
1               5                   10
```

<210> SEQ ID NO 7
<211> LENGTH: 14
<212> TYPE: PRT
<213> ORGANISM: Artificial Sequence
<220> FEATURE:
<223> OTHER INFORMATION: PLP178-191

<400> SEQUENCE: 7

```
Asn Thr Trp Thr Thr Cys Gln Ser Ile Ala Phe Pro Ser Lys
1               5                   10
```

<210> SEQ ID NO 8
<211> LENGTH: 65
<212> TYPE: DNA
<213> ORGANISM: Artificial Sequence
<220> FEATURE:
<223> OTHER INFORMATION: PLP (178-191)

<400> SEQUENCE: 8
ctggagacca gaatacctgg accacctgcc agtctattgc cttccctagc aagtctagat    60
agcta                                                                65

<210> SEQ ID NO 9
<211> LENGTH: 63
<212> TYPE: DNA
<213> ORGANISM: Artificial Sequence
<220> FEATURE:
<223> OTHER INFORMATION: PLP (139-151)

<400> SEQUENCE: 9
ctcgagacca tgcattgttt gggaaaatgg ctaggacatc ccgacaagtt ttctagatag    60
cta                                                                 63

-continued

```
<210> SEQ ID NO 10
<211> LENGTH: 63
<212> TYPE: DNA
<213> ORGANISM: Artificial Sequence
<220> FEATURE:
<223> OTHER INFORMATION: PLP (139-151) L144/R147

<400> SEQUENCE: 10
ctcgagacca tgcattgttt gggaaaacta ctaggacgcc ccgacaagtt ttctagatag      60
cta                                                                    63

<210> SEQ ID NO 11
<211> LENGTH: 13
<212> TYPE: PRT
<213> ORGANISM: Homo sapiens

<400> SEQUENCE: 11

Val His Phe Phe Lys Asn Ile Val Thr Pro Arg Thr Pro
 1               5                  10

<210> SEQ ID NO 12
<211> LENGTH: 7
<212> TYPE: PRT
<213> ORGANISM: Homo sapiens

<400> SEQUENCE: 12

Phe Lys Asn Ile Val Thr Pro
 1               5

<210> SEQ ID NO 13
<211> LENGTH: 153
<212> TYPE: PRT
<213> ORGANISM: Artificial Sequence
<220> FEATURE:
<223> OTHER INFORMATION: amino acid sequence of a Th2 cytokine

<400> SEQUENCE: 13

Met Gly Leu Thr Ser Gln Leu Leu Pro Pro Leu Phe Phe Leu Leu Ala
 1               5                  10                  15

Cys Ala Gly Asn Phe Val His Gly His Lys Cys Asp Ile Thr Leu Gln
            20                  25                  30

Glu Ile Ile Lys Thr Leu Asn Ser Leu Thr Glu Gln Lys Thr Leu Cys
        35                  40                  45

Thr Glu Leu Thr Val Thr Asp Ile Phe Ala Ala Ser Lys Asn Thr Thr
    50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                85                  90                  95

Phe His Arg His Lys Gln Leu Ile Arg Phe Leu Lys Arg Leu Asp Arg
            100                 105                 110

Asn Leu Trp Gly Leu Ala Gly Leu Asn Ser Cys Pro Val Lys Glu Ala
        115                 120                 125

Asn Gln Ser Thr Leu Glu Asn Phe Leu Glu Arg Leu Lys Thr Ile Met
    130                 135                 140

Arg Glu Lys Tyr Ser Lys Cys Ser Ser
145                 150

<210> SEQ ID NO 14
<211> LENGTH: 614
```

```
<212> TYPE: DNA
<213> ORGANISM: Artificial Sequence
<220> FEATURE:
<223> OTHER INFORMATION: sequence encoding a Th2 cytokine
<220> FEATURE:
<221> NAME/KEY: CDS
<222> LOCATION: (64)...(525)
<220> FEATURE:
<221> NAME/KEY: mat_peptide
<222> LOCATION: (136)...(522)

<400> SEQUENCE: 14
gatcgttagc ttctcctgat aaactaattg cctcacattg tcactgcaaa tcgacaccta      60 tta atg ggt ctc acc tcc caa ctg ctt ccc cct ctg ttc ttc ctg cta      108
    Met Gly Leu Thr Ser Gln Leu Leu Pro Pro Leu Phe Phe Leu Leu
     1               5                  10                  15 gca tgt gcc ggc aac ttt gtc cac gga cac aag tgc gat atc acc tta      156
Ala Cys Ala Gly Asn Phe Val His Gly His Lys Cys Asp Ile Thr Leu
                 20                  25                  30 cag gag atc atc aaa act ttg aac agc ctc aca gag cag aag act ctg      204
Gln Glu Ile Ile Lys Thr Leu Asn Ser Leu Thr Glu Gln Lys Thr Leu
             35                  40                  45 tgc acc gag ttg acc gta aca gac atc ttt gct gcc tcc aag aac aca      252
Cys Thr Glu Leu Thr Val Thr Asp Ile Phe Ala Ala Ser Lys Asn Thr
         50                  55                  60 act gag aag gaa acc ttc tgc agg gct gcg act gtg ctc cgg cag ttc      300
Thr Glu Lys Glu Thr Phe Cys Arg Ala Ala Thr Val Leu Arg Gln Phe
 65                  70                  75 tac agc cac cat gag aag gac act cgc tgc ctg ggt gcg act gca cag      348
Tyr Ser His His Glu Lys Asp Thr Arg Cys Leu Gly Ala Thr Ala Gln
 80                  85                  90                  95 cag ttc cac agg cac aag cag ctg atc cga ttc ctg aaa cgg ctc gac      396
Gln Phe His Arg His Lys Gln Leu Ile Arg Phe Leu Lys Arg Leu Asp
                100                 105                 110 agg aac ctc tgg ggc ctg gcg ggc ttg aat tcc tgt cct gtg aag gaa      444
Arg Asn Leu Trp Gly Leu Ala Gly Leu Asn Ser Cys Pro Val Lys Glu
            115                 120                 125 gcc aac cag agt acg ttg gaa aac ttc ttg gaa agg cta aag acg atc      492
Ala Asn Gln Ser Thr Leu Glu Asn Phe Leu Glu Arg Leu Lys Thr Ile
        130                 135                 140 atg aga gag aaa tat tca aag tgt tcg agc tga atattttaat ttatgagttt    545
Met Arg Glu Lys Tyr Ser Lys Cys Ser Ser *
    145                 150 ttgatagctt tatttttaa gtatttatat atttataact catcataaaa taaagtatat      605
atagaatct                                                              614

<210> SEQ ID NO 15
<211> LENGTH: 15
<212> TYPE: PRT
<213> ORGANISM: Artificial Sequence
<220> FEATURE:
<223> OTHER INFORMATION: HSVP16 P45

<400> SEQUENCE: 15

Asp Met Thr Pro Ala Asp Ala Leu Asp Asp Arg Asp Leu Glu Met
 1               5                  10                  15

<210> SEQ ID NO 16
<211> LENGTH: 39
<212> TYPE: DNA
<213> ORGANISM: Artificial Sequence
<220> FEATURE:
<223> OTHER INFORMATION: oligonucleotide primer
```

<400> SEQUENCE: 16
cgcggatcct tgatgggtct caaccccag ctagttgtc       39

<210> SEQ ID NO 17
<211> LENGTH: 38
<212> TYPE: DNA
<213> ORGANISM: Artificial Sequence
<220> FEATURE:
<223> OTHER INFORMATION: oligonucleotide primer

<400> SEQUENCE: 17
acgctcgagg tactacgagt aatccatttg catgatgc       38

<210> SEQ ID NO 18
<211> LENGTH: 72
<212> TYPE: DNA
<213> ORGANISM: Artificial Sequence
<220> FEATURE:
<223> OTHER INFORMATION: insulin A (+) strand
<220> FEATURE:
<221> NAME/KEY: modified_base
<222> LOCATION: 68
<223> OTHER INFORMATION: q
<220> FEATURE:
<221> NAME/KEY: misc_feature
<222> LOCATION: 68
<223> OTHER INFORMATION: n = A,T,C or G

<400> SEQUENCE: 18
ccggaattcg ccatgtgcac gtcaatctgt tcactgtacc agctagagaa ctactgcaac       60
tagtctanga gc       72

<210> SEQ ID NO 19
<211> LENGTH: 70
<212> TYPE: DNA
<213> ORGANISM: Artificial Sequence
<220> FEATURE:
<223> OTHER INFORMATION: insulin B (+) strand

<400> SEQUENCE: 19
ccggaattcg ccatgagcca cctagtagaa gcactaacct cgtatgcggc gaacgaggtt       60
agtctagagc       70

<210> SEQ ID NO 20
<211> LENGTH: 15
<212> TYPE: PRT
<213> ORGANISM: Artificial Sequence
<220> FEATURE:
<223> OTHER INFORMATION: insulin A (7-21) peptide

<400> SEQUENCE: 20

Cys Thr Ser Ile Cys Ser Leu Tyr Gln Leu Glu Asn Tyr Cys Asn
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: insulin B (9-23) peptide

<400> SEQUENCE: 21

Ser His Leu Val Glu Ala Leu Tyr Leu Val Cys Gly Glu Arg Gly
1               5                   10                  15

```
<210> SEQ ID NO 22
<211> LENGTH: 15
<212> TYPE: PRT
<213> ORGANISM: Artificial Sequence
<220> FEATURE:
<223> OTHER INFORMATION: control peptide p43 derived from Bacillus
      subtilis hype protein X13

<400> SEQUENCE: 22

Arg Lys Val Val Thr Asp Phe Phe Lys Asn Ile Pro Gln Arg Ile
 1               5                  10                  15

<210> SEQ ID NO 23
<211> LENGTH: 15
<212> TYPE: DNA
<213> ORGANISM: Artificial Sequence
<220> FEATURE:
<223> OTHER INFORMATION: IL-4 primer

<400> SEQUENCE: 23
catcggcatt ttgaa                                                     15

<210> SEQ ID NO 24
<211> LENGTH: 20
<212> TYPE: DNA
<213> ORGANISM: Artificial Sequence
<220> FEATURE:
<223> OTHER INFORMATION: IL-4 primer

<400> SEQUENCE: 24
cgtttggcac atccatctcc                                                20

<210> SEQ ID NO 25
<211> LENGTH: 23
<212> TYPE: DNA
<213> ORGANISM: Artificial Sequence
<220> FEATURE:
<223> OTHER INFORMATION: IL-4 probe

<400> SEQUENCE: 25
cacaggagaa gggacgccat gca                                            23

<210> SEQ ID NO 26
<211> LENGTH: 19
<212> TYPE: DNA
<213> ORGANISM: Artificial Sequence
<220> FEATURE:
<223> OTHER INFORMATION: IFN-gamma primer

<400> SEQUENCE: 26
tcctgcggcc tagctctga                                                 19

<210> SEQ ID NO 27
<211> LENGTH: 16
<212> TYPE: DNA
<213> ORGANISM: Artificial Sequence
<220> FEATURE:
<223> OTHER INFORMATION: IFN-gamma primer

<400> SEQUENCE: 27
gccatgagga agagct                                                    16

<210> SEQ ID NO 28
<211> LENGTH: 29
<212> TYPE: DNA
<213> ORGANISM: Artificial Sequence
```

```
<220> FEATURE:
<223> OTHER INFORMATION: IFN-gamma probe

<400> SEQUENCE: 28
acaatgaacg ctacacactg catcttggc                                          29

<210> SEQ ID NO 29
<211> LENGTH: 20
<212> TYPE: DNA
<213> ORGANISM: Artificial Sequence
<220> FEATURE:
<223> OTHER INFORMATION: IL-10 primer

<400> SEQUENCE: 29
tgcagcagct cagagggttc                                                    20

<210> SEQ ID NO 30
<211> LENGTH: 20
<212> TYPE: DNA
<213> ORGANISM: Artificial Sequence
<220> FEATURE:
<223> OTHER INFORMATION: IL-10 primer

<400> SEQUENCE: 30
ctggccacag ttttcaggga                                                    20

<210> SEQ ID NO 31
<211> LENGTH: 25
<212> TYPE: DNA
<213> ORGANISM: Artificial Sequence
<220> FEATURE:
<223> OTHER INFORMATION: IL-10 probe

<400> SEQUENCE: 31
cctactgtca tcccccagcc gcttc                                              25

<210> SEQ ID NO 32
<211> LENGTH: 24
<212> TYPE: DNA
<213> ORGANISM: Artificial Sequence
<220> FEATURE:
<223> OTHER INFORMATION: TGF-beta primer

<400> SEQUENCE: 32
gcaacatgtg gaactctacc agaa                                               24

<210> SEQ ID NO 33
<211> LENGTH: 21
<212> TYPE: DNA
<213> ORGANISM: Artificial Sequence
<220> FEATURE:
<223> OTHER INFORMATION: TGF-beta primer

<400> SEQUENCE: 33
gacgtcaaaa gacagccact c                                                  21

<210> SEQ ID NO 34
<211> LENGTH: 24
<212> TYPE: DNA
<213> ORGANISM: Artificial Sequence
<220> FEATURE:
<223> OTHER INFORMATION: TGF-beta probe

<400> SEQUENCE: 34
accttggtaa ccggctgctg accc                                               24
```

DNA VACCINATION FOR TREATMENT OF MULTIPLE SCLEROSIS AND INSULIN-DEPENDENT DIABETES MELLITUS

CROSS-REFERENCES

This application claims priority to earlier filed International Patent Application Serial No. PCT/US00/06233, filed Mar. 10, 2000 which application claims priority to U.S. patent application Ser. No. 09/267,590 filed Mar. 12, 1999, both of which applications are incorporated herein by reference in their entirety.

STATEMENT AS TO RIGHTS TO INVENTIONS MADE UNDER FEDERALLY-SPONSORED RESEARCH OR DEVELOPMENT

This invention was made with Government support under contract NS18235 awarded by the National Institutes of Health. The Government has certain rights in this invention.

INTRODUCTION

The complexity of the immune system has been a daunting barrier to an understanding of immune system dysfunction. In recent years, the techniques of molecular biology have provided insight into the mechanisms and components that underlie immunity. To a large extent, the story of immunity is the story of lymphocytes. Lymphocytes possess an extremely complex and subtle system for interacting with each other, with antigen-presenting cells, and with foreign antigens and cells.

Modulation of the immune response varies with the specific factors produced, and the receptors present on the responding cell. The pathways for down-regulating responses are as important as those required for activation. T cell tolerance is one well-known mechanism for preventing an immune response to a particular antigen. Other mechanisms, such as secretion of suppressive cytokines, are also known.

A common feature in a number of diseases and inflammatory conditions is the involvement of pro-inflammatory CD4$^+$ T cells. These T cells are responsible for the release of inflammatory, Th1 type cytokines. Cytokines characterized as Th1 type include interleukin 2 (IL-2), γ-interferon, TNFα and IL-12. Such pro-inflammatory cytokines act to stimulate the immune response, in many cases resulting in the destruction of autologous tissue. Cytokines associated with suppression of T cell response are the Th2 type, and include IL-10, IL-4 and TGF-β. It has been found that Th1 and Th2 type T cells may use the identical antigen receptor in response to an immunogen; in the former producing a stimulatory response and in the latter a suppressive response.

Cytokines play a critical role in the development and recovery from autoimmune diseases. Th1 cytokines such as interleukin 12 (IL-12) and interferon gamma (IFNγ) have been found in the central nervous system (CNS) of multiple sclerosis (MS) patients as well as in animals with EAE (Issazadeh et al. (1995). *J Neuroimmunol* 61:205-12). Th2 cytokines such as IL-4, IL-5 and IL-10 have been found to be elevated either during remission of MS or EAE (Waisman et al. (1997) Immunointervention in autoimmunity by Th1/Th2 regulation, L. Adorini, ed. (Austin, Tex.: R.G. Landes Co.), pp. 129-50). Previous studies have shown that systemic administration of IL-4 as well as local CNS administration of IFNγ can reduce the severity of EAE (Racke et al. (1994) *J Exp Med* 180:1961-6; Voorthuis et al. (1990) *Clin Exp Immunol* 81:183-8). Furthermore, the addition of IL-4 to naive T cells can result in the development of Th2 type cells, whereas the addition of IL-12 can result in the development of Th1 type cells (Macatonia et al. (1993) *Int Immunol* 5:1119-28).

DNA vaccination is effective in protecting experimental animals against infectious pathogens and cancer, and recently has been used to prevent autoimmune disease (Waisman et al. (1996) *Nat Med* 2, 899-905). Experimental autoimmune encephalomyelitis (EAE), a prototypic animal model of T cell autoimmunity, reflects many of the clinical and pathologic features of the human disease, multiple sclerosis.

In order to modify immune responses to DNA vaccines, DNA co-vaccination has been performed with cytokine genes, along with the genes for certain pathogens. Examples include DNA immunization with hepatitis B virus antigens and IL-2 DNA which enhanced Th1 responses, HIV antigens with IL-12 DNA which enhanced cytotoxic T cell activity, and influenza antigens with IL-6 DNA which enhanced antiviral activity (see, for example, Chow et al. (1998) *J Immunol* 160(3):1320-9).

Vaccination of mice with naked DNA that encodes the predominant T cell receptor (TCR) β chain that is rearranged in myelin basic protein (MBP) reactive T cells, has been shown to protect mice from EAE. Such immunization induced a pattern of Th2 cytokine production by myelin reactive T cells, creating a suppressive environment blocking autoimmunity: T cells reacting to the myelin autoantigen deviated from an aggressive T helper 1 (Th1) type to a suppressive Th2 type.

Further development of treatment that specifically inhibits T cell activation would be of great medical benefit.

Relevant Literature

Waisman et al. (1996) *Nat. Med.* 2:899-905 and) Offner et al. (1998) *J. Immunol.* 161:2178-2186 describe the use of DNA vaccination to prevent experimental autoimmune encehalomyelitis (EAE). The injection of DNA to promote vaccination against microbes and tumors is discussed in Cohen et al. (1997) *Hosp. Pract.* 32:169-171; Syrengelas, et al. (1996) *Nat. Med.* 2:1038-1041; Ulmer et al. (1996) *Curr Opin Immunol.* 8:531-536; Pardoll et al. (1995) *Immunity* 3:165-169; Davis et al. (1993) *Hum. Mol. Genet.* 2:1847-1851; Ulmer et al., (1993) *Science* 259:1745-1749; and Tang et al. (1992) *Nature* 356:152-154. Genetic immunization has demonstrated induction of both a specific humoral but also a more broadly reacting cellular immune response in animal models of cancer, mycoplasma, TB, malaria, and many virus infections, including influenza and HIV. See, for example, Mor et al. (1995) *J Immunol* 155:203946; Xu and Liew (1995) *Immunology* 84:173-6; and Davis et al. (1994) *Vaccine* 12:1503-9.

Susceptibility to multiple sclerosis (MS) has been associated with certain MHC Class II genes, Oksenberg and Steinman (1990) *Current Opinion in Immunology* 2:619-621. At the cellular level, oligoclonality of T-cells has been described in the cerebrospinal fluid (CSF) of MS patients, Lee et al., *Ann. Neurol.* 29:3340 (1991).

CNS antigens, including myelin proteins, studied in the context of MS are discussed in de Rosbo et al., J. Autoimmunity 11:287-299 (1998). Enhancers of the immune response to DNA vaccines include unmethylated CpG dinucleotides, Krieg et al. (1998) *Trends Microbiol.* 6:23-27, and fused pathogen-derived sequences, King et al. (1998) *Nat. Med.* 4:1281-1286.

SUMMARY OF THE INVENTION

Methods are provided for the suppression of pro-inflammatory T cell responses in autoimmune disease. A mammalian host is vaccinated with a DNA expression vector encoding an autoantigen fragment. In response to the vaccination, pathogenic T cell proliferation is inhibited and production of Th1 cytokines, including IL-2, IL-10, IFN-γ and IL-15 is reduced. In one embodiment of the invention, a nucleic acid encoding a Th2 cytokine is co-administered with the autoantigen coding sequence. The use of IL-4 coding sequences is of particular interest. Suppressive vaccination diminishes T cell pro-inflammatory responses in a specific, targeted manner. Conditions that benefit from this treatment include autoimmune diseases, tissue transplantation and other diseases associated with inflammation.

BRIEF DESCRIPTION OF THE DRAWINGS

FIG. 6. Quantitative PCR measurement of cytokine expression by pancreatic lymph node cells from vaccinated NOD mice cultured with 10 μg/ml insulin B (9-23) peptide. PcDNA control vaccinated levels (solid bars) were used as a standard against which the insB-PcDNA vaccinated values (hatched bars) were compared.

DESCRIPTION OF THE SPECIFIC EMBODIMENTS

Figure 1:
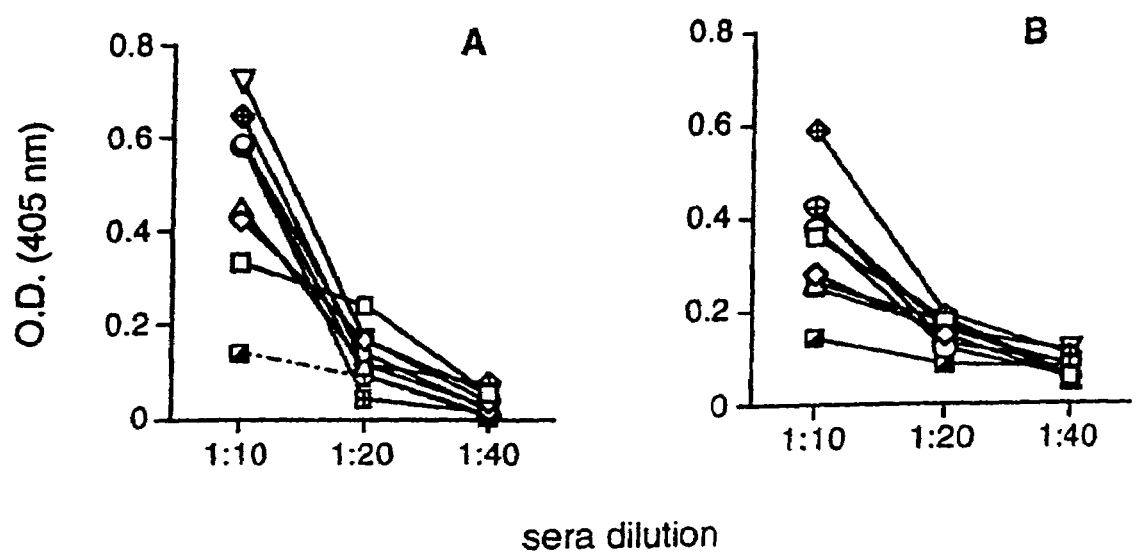
FIG. 1. Anti-SCH IgG (A) and anti-PLP139-151 (B) antibody titers in SJL/J mice after DNA immunization with the PLP minigene.

The subject methods provide a means for therapeutic treatment and investigation of inflammation, through the suppression of pathogenic antigen-specific T-cell responses. A DNA expression cassette is injected into host tissue, for example muscle or skin. The vector comprises a DNA sequence encoding at least a portion of an autoantigen. The vaccination may also include DNA sequences encoding a Th2 cytokine, e.g. IL-4. In response to this vaccination, a suppressive response is evoked. Antigen-specific T cell proliferation is inhibited and Th1 cytokine production is reduced.

Without limiting the scope of the invention, it is believed that the methods described herein are a novel method of protective immunity, which combines the effects of DNA vaccination and local gene delivery. After DNA vaccination with a autoantigen epitope alone, T cells are anergic. This may be in part due to the biological effects of DNA motifs like unmethylated CpG dinucleotides in particular base contexts (CpG-S motifs) (Krieg et al. (1998) *Trends in Microbiol.* 6:23-27). The addition of IL4 as a DNA co-vaccine rescues the anergy imposed by the autoantigen DNA vaccine, and drives the response to a Th2 phenotype. STAT6 is activated in draining lymph node cells by the IL4 DNA vaccine. It is believed that IL4 is produced from the DNA vaccine administered and that it interacts with IL4 receptor on lymph node cells, which in turn causes the activation of STAT6 downstream of the receptor. Immunization against the antigens that trigger those autoimmune diseases caused by Th1 autoreactive cells, diseases such as multiple sclerosis, juvenile diabetes and rheumatoid arthritis, would be conditions where co-vaccination with DNA encoding IL-4 might prove beneficial Autbantigens, as used herein, are endogenous proteins or fragments thereof that elicit a pathogenic immune response. Of particular interest are autoantigens that induce a T cell mediated inflammatory pathogenic response. Suppressive vaccination with the relevant target autoantigen finds use in the treatment of autoimmune diseases characterized by the involvement of pro-inflammatory T cells, such as multiple sclerosis, experimental autoimmune encephalitis, rheumatoid arthritis and insulin dependent diabetes mellitus. Animal models, particularly small mammals, e.g. murine, lagomorpha, etc. are of interest for experimental investigations.

The subject methods of suppressive immunization are used for prophylactic or therapeutic purposes. Use used herein, the term "treating" is used to refer to both prevention of disease, and treatment of pre-existing conditions. The prevention of autoimmune disease involving the vaccine autoantigen (VA), is accomplished by administration of the vaccine prior to development of overt disease. The treatment of ongoing disease, where the suppressive vaccination stabilizes or improves the clinical symptoms of the patient, is of particular interest. Such treatment is desirably performed prior to complete loss of function in the affected tissues.

Autoantigens known to be associated with disease include myelin proteins with demyelinating diseases, e.g. multiple sclerosis and experimental autoimmune myelitis; collagens and rheumatoid arthritis; insulin, proinsulin, glutamic acid decarboxylase 65 (GAD65); islet cell antigen (ICA512; ICA12) with insulin dependent diabetes. An association of GAD epitopes with diabetes is described in a number of publications, including U.S. Pat. No. 5,212,447; and European patent application no. 94.927940.0. An association of insulin epitopes with autoimmune insulitis is described in Griffin et al. (1995) *Am. J. Pathol.* 147:845-857. Rudy et al. (1995) *Mol. Med.* 1:625-633 disclose an epitope that is similar in GAD and proinsulin.

The protein components of myelin proteins, including myelin basic protein (MBP), proteolipid protein (PLP), myelin-associated glycoprotein (MAG) and myelin oligodendrocyte glycoprotein (MOG), are of particular interest for use as immunogens of the invention. The suppression of T cell responsiveness to these antigens is used to prevent or treat demyelinating diseases.

In one embodiment of the invention, the vaccine autoantigen is proteolipid. For convenience, a reference sequence of human PLP is provided as SEQ ID NO:1; and human myelin basic protein as SEQ ID NO:3. Proteolipid is a major constituent of myelin, and is known to be involved in demyelinating diseases (see, for example Greer et al. (1992) *J. Immunol.* 149:783-788 and Nicholson (1997) *Proc. Natl. Acad. Sci. USA* 94:9279-9284).

The integral membrane protein PLP is a dominant autoantigen of myelin. Determinants of PLP antigenicity have been identified in several mouse strains, and include residues 139-151 (Tuohy et al. (1989) *J. Immunol.* 142:1523-1527), 103-116 (Tuohy et al., (1988) *J. Immunol.* 141:1126-1130], 215-232 (Endoh et al. (1990) *Int. Arch. Allergy Appl. Immunol.* 92:433-438), 43-64 (Whitham et al., (1991) *J. Immunol.* 147: 3803-3808) and 178-191 (Greer, et al. (1992) *J. Immunol.* 149:783-788). Immunization with native PLP or with synthetic peptides corresponding to PLP epitopes induces EAE. Analogues of PLP peptides generated by amino acid substitution can prevent EAE induction and progression (Kuchroo et al. (1994) J. Immunol. 153:3326-3336, Nicholson et al. (1997) *Proc. Natl. Acad. Sci. USA* 94:9279-9284).

MBP is an extrinsic myelin protein that has been studied extensively. At least 26 MBP epitopes have been reported (Meinl et al. (1993) *J. Clin. Invest.* 92:2633-2643). Of particular interest for use in the present invention are residues 1-11, 59-76 and 87-99. Analogues of MBP peptides generated by truncation have been shown to reverse EAE (Karin et al., (1998) J. Immunol. 160:5188-5194). DNA encoding polypeptide fragments may comprise coding sequences for immunogenic epitopes, e.g. myelin basic protein p84-102, more particularly myelin basic protein p87-99, (SEQ ID NO:11) VHFFKNIVTPRTP (p87-99), or even the truncated 7-mer peptide (SEQ ID NO:12) FKNIVTP. The sequences of myelin basic protein exon 2, including the immunodominant epitope bordered by amino acids 59-85, are also of interest. For examples, see Sakai et al. (1988) *J Neuroimmunol* 19:21-32; Baxevanis et al (1989) *J Neuroimmunol* 22:23-30; Ota et al (1990) *Nature* 346:183-187; Martin et al (1992) *J. Immunol.* 148:1350-1366, Valli et al (1993) *J Clin Inv* 91:616. The immunodominant MBP(84-102) peptide has been found to bind with high affinity to DRB1*1501 and DRB5*0101 molecules of the disease-associated DR2 haplotype. Overlapping but distinct peptide segments were important for binding to these molecules; hydrophobic residues (Val189 and Phe92) in the MBP (88-95) segment for peptide binding to DRB1*1501 molecules; hydrophobic and charged residues (Phe92, Lys93) in the MBP (89-101/102) sequence contributed to DRB5*0101 binding.

The transmembrane glycoprotein MOG is a minor component of myelin that has been shown to induce EAE. Immunodominant MOG epitopes that have been identified in several mouse strains include residues 1-22, 35-55, 64-96 (deRosbo et al. (1998) J. Autoimmunity 11:287-299, deRosbo et al. (1995) Eur J. Immunol. 25:985-993) and 41-60 (Leadbetter et al. (1998) J Immunol 161:504-512).

For the treatment of diabetes, immunogens of interest include IA-2; IA-2beta; GAD; insulin; proinsulin; HSP; glima 38; ICA69; and p52. For example, insulin (which sequence is publicly available, for example from Sures et al. (1980) *Science* 208:57-59; Bell et al. (1979) *Nature* 282:525-527; and Bell et al. (1980) *Nature* 284:26-32) has been found to have immunodominant epitopes in the B chain, e.g. residues 9-23; as well as in the pre-proinsulin leader sequence. Other autoantigens associated with diabetes include glutamic acid decarboxylase 65 (GAD65), e.g. residues 206-220; 221-235, 286-300; 456-470; and peptides including residues p247, p509; p524 (Kauffman et al. (1993) Nature 366:69-72).

A DNA expression cassette encoding at least a portion of an autoantigen, usually as part of a vector, is introduced into tissue of the vaccine recipient. The minigene is expressed in the tissue, and the encoded polypeptide acts as an immunogen, or antigen. The autoantigen sequence may be from any mammalian or avian species, e.g. primate sp., particularly humans; rodents, including mice, rats and hamsters; rabbits; equines, bovines, canines, felines; etc. Of particular interest are the human and mouse autoantigen segments. Generally, the sequence will have the same species of origin as the animal host, preferably it will be autologous The subject DNA expression cassette will comprise most or all of the sequence encoding an autoantigen fragment, as defined by Kabat et al., supra. The coding sequence may be truncated at the 5' or 3' terminus and may be a fragment of the complete polypeptide sequence. In one embodiment of the invention, the sequence encodes a peptide fragment that is known to be presented to pathogenic T cells, for example peptides presented by Class II MHC molecules of the host. Such peptides have been described in the literature, and are typically of about 8 to about 30 amino acids in length.

The vaccine may be formulated with one or a cocktail of autoantigen sequences. While it has been found that a single sequence is capable of suppressing a response to multiple epitopes, it may be desirable in some cases to include multiple sequences, where each encodes a different epitope. For example, see Leadbetter et al. (1998) J. Immunol. 161:504-512. A formulation comprised of multiple coding sequences of distinct PLP epitopes may be used to induce a more potent and/or sustained suppressive response. By specifically targeting multiple autoreactive T cell populations, such a formulation may slow or prevent the development of autoantigen resistance. The use of PLP sequences in combination with other myelin protein epitopes may effectively suppress the repertoire of myelin-reactive T cells. Similar autoantigen combinations to suppress autoimmune response, e.g., glutamic acid decarboxylase (GAD) and pancreatic islet cell autoantigen for the treatment of insulin dependent diabetes, are contemplated.

In addition to the specific epitopes and polypeptides of autoantigens, the immune response may be enhanced by the inclusion of CpG sequences, as described by Krieg et al. (1998) *Trends Microbiol.* 6:23-27, and helper sequence, King et al. (1998) *Nat. Med.* 4:1281-1286. Biological effects of DNA motifs like unmethylated CpG dinucleotides in particular base contexts (CPG-S motifs) may modulate innate immune responses when injected to animals. Low numbers of CpG motifs, or the presence of imperfect motifs, may act in the development of anergy by immunization with autoantigens.

The polypeptide coding sequence, which may be autoantigen or cytokine, sequences are inserted into an appropriate expression cassette. The expression construct is prepared in conventional ways. The cassette will have the appropriate transcriptional and translational regulatory sequences for expression of the sequence in the vaccine recipient cells. The cassette will generally be a part of a vector, which contains a suitable origin of replication, and such genes encoding selectable markers as may be required for growth, amplification and manipulation of the vector, prior to its introduction into the recipient. Suitable vectors include plasmids, YACs, BACs, bacteriophage, retrovirus, and the like. Conveniently, the expression vector will be a plasmid. Prior to vaccination, the cassette may be isolated from vector sequences by cleavage, amplification, etc. as known in the art. For injection, the DNA may be supercoiled or linear, preferably supercoiled. The cassette may be maintained in the host cell for extended periods of time, or may be transient, generally transient. Stable maintenance is achieved by the inclusion of sequences that provide for integration and/or maintenance, e.g. retroviral vectors, EBV vectors and the like.

The expression cassette will generally employ an exogenous transcriptional initiation region, i.e. a promoter other than the promoter which is associated with the T cell receptor in the normally occurring chromosome. The promoter is functional in host cells, particularly host cells targeted by the cassette. The promoter may be introduced by recombinant methods in vitro, or as the result of homologous integration of the sequence by a suitable host cell. The promoter is operably linked to the coding sequence of the autoantigen to produce a translatable mRNA transcript. Expression vectors conveniently will have restriction sites located near the promoter sequence to facilitate the insertion of autoantigen sequences.

Expression cassettes are prepared comprising a transcription initiation region, which may be constitutive or inducible, the gene encoding the autoantigen sequence, and a transcriptional termination region. The expression cassettes may be introduced into a variety of vectors. Promoters of interest may be inducible or constitutive, usually constitutive, and will provide for high levels of transcription in the vaccine recipient cells. The promoter may be active only in the recipient cell type, or may be broadly active in many different cell types. Many strong promoters for mammalian cells are known in the art, including the β-actin promoter, SV40 early and late promoters, immunoglobulin promoter, human cytomegalovirus promoter, retroviral LTRs, etc. The promoters may or may not be associated with enhancers, where the enhancers may be naturally associated with the particular promoter or associated with a different promoter.

A termination region is provided 3' to the coding region, where the termination region may be naturally associated with the variable region domain or may be derived from a different source. A wide variety of termination regions may be employed without adversely affecting expression.

The various manipulations may be carried out in vitro or may be performed in an appropriate host, e.g. *E. coli*. After each manipulation, the resulting construct may be cloned, the vector isolated, and the DNA screened or sequenced to ensure the correctness of the construct. The sequence may be screened by restriction analysis, sequencing, or the like.

A small number of nucleotides may be inserted at the terminus of the autoantigen sequence, usually not more than 20, more usually not more than 15. The deletion or insertion of nucleotides will usually be as a result of the needs of the construction, providing for convenient restriction sites, addition of processing signals, ease of manipulation, improvement in levels of expression, or the like. In addition, one may wish to substitute one or more amino acids with a different amino acid for similar reasons, usually not substituting more than about five amino acids in the region.

In one embodiment of the invention the autoantigen is co-vaccinated with DNA sequences encoding a Th2 cytokine, which group includes IL-4, IL-10, TGF-β, etc. IL4 is of particular interest. The lymphokine IL-4 has T-cell and mast cell growth factor activities. Human IL4 is an 18-kD glycoprotein. For convenience the amino acid sequence is provided herein as SEQ ID NO:13, and the DNA sequence as SEQ ID NO:14 (Yokota et al. (1986) *P.N.A.S.* 83:5894-5898). This sequence is the preferred sequence of the invention. However, the invention is not limited to the use of this sequence in constructs of the invention. Also of use are closely related variant sequences that have the same biological activity, or substantially similar biological activity. A specific STAT6 DNA-binding target site is found in the promoter of the IL4 receptor gene; and STAT6 activates IL4 gene expression via this site. Interferons inhibit IL4-induced activation of STAT6 and STAT6-dependent gene expression, at least in part, by inducing expression of SOCS1 (see Kotanides et al. (1996) *J. Biol. Chem.* 271:25555-25561).

Variant sequences encode protein subunits which, when present in a DNA construct of the invention, give the protein one or more of the biological properties of IL-4 as described above. DNA sequences of the invention may differ from a native IL-4 sequence by the deletion, insertion or substitution of one or more nucleotides, provided that they encode a protein with the appropriate biological activity as described above. Similarly, they may be truncated or extended by one or more nucleotides. Alternatively, DNA sequences suitable for the practice of the invention may be degenerate sequences that encode the naturally occurring IL-4 protein. Typically, DNA sequences of the invention have at least 70%, at least 80%, at least 90%, at least 95% or at least 99% sequence identity to a native IL-4 coding sequence. They may originate from any species, though DNAs encoding human proteins are preferred. Variant sequences may be prepared by any suitable means known in the art.

With respect of substitutions, conservative substitutions are preferred. Typically, conservative substitutions are substitutions in which the substituted amino acid is of a similar nature to the one present in the naturally occurring protein, for example in terms of charge and/or size and/or polarity and/or hydrophobicity. Similarly, conservative substitutions typically have little or no effect on the activity of the protein. Proteins of the invention that differ in sequence from naturally occurring IL-4 may be engineered to differ in activity from naturally occurring IL-4. Such manipulations will typically be carried out at the nucleic acid level using recombinant techniques, as known in the art.

The vaccine may be formulated with one or a cocktail of autoantigen sequences, which may be on the same or different vectors. The DNA vectors are suspended in a physiologically acceptable buffer, generally an aqueous solution e.g. normal saline, phosphate buffered saline, water, etc. Stabilizing agents, wetting and emulsifying agents, salts for varying the osmotic pressure or buffers for securing an adequate pH value, and skin penetration enhancers can be used as auxiliary agents. The DNA will usually be present at a concentration of at least about 1 ng/ml and not more than about 10 mg/ml, usually at about from 100 μg to 1 mg/ml.

In some embodiments of the the present invention, the patient is administered both an autoantigen encoding sequence and a Th2 cytokine encoding sequence. The cytokine and autoantigen can be delivered simultaneously, or within a short period of time, by the same or by different routes. In one embodiment of the invention, the two sequences are co-formulated, meaning that they are delivered together as part of a single composition. The coding sequences may be associated with one another by covalent linkage in a single nucleic acid molecule, where they may be present as two distinct coding sequences separated by a translational stop, or may be be present as a single fusion protein. The two sequences may also by joined by non-covalent interaction such as hydrophobic interaction, hydrogen bonding, ionic interaction, van der Waals interaction, magnetic interaction, or combinations thereof. Alternatively, the two constructs may simply be mixed in a common suspension, or encapsulated together in some form of delivery device such as, for example, an alginate device, a liposome, chitosan vesicle, etc. (see, for example, WO 98/33520, incorporated herein by reference).

The vaccine may be fractionated into two or more doses, of at least about 1 μg, more usually at least about 100 μg, and preferably at least about 1 mg per dose, administered from about 4 days to one week apart. In some embodiments of the invention, the individual is subject to a series of vaccinations to produce a full, broad immune response. According to this method, at least two and preferably four injections are given over a period of time. The period of time between injections may include from 24 hours apart to two weeks or longer between injections, preferably one week apart. Alternatively, at least two and up to four separate injections are given simultaneously at different parts of the body.

The DNA vaccine is injected into muscle or other tissue subcutaneously, intradermally, intravenously, orally or directly into the spinal fluid. Of particular interest is injection into skeletal muscle. The genetic vaccine may be administered directly into the individual to be immunized or ex vivo into removed cells of the individual which are reimplanted after administration. By either route, the genetic material is introduced into cells which are present in the body of the individual. Alternatively, the genetic vaccine may be introduced by various means into cells that are removed from the individual. Such means include, for example, transfection, electroporation and microprojectile bombardment. After the genetic construct is taken up by the cells, they are reimplanted into the individual. Otherwise non-immunogenic cells that have genetic constructs incorporated therein can be taken from one individual and implanted into another.

An example of intramuscular injection may be found in Wolff et al. (1990) *Science* 247:1465-1468. Jet injection may also be used for intramuscular administration, as described by Furth et al. (1992) *Anal Biochem* 205:365-368. The DNA may be coated onto gold microparticles, and delivered intradermally by a particle bombardment device, or "gene gun". Microparticle DNA vaccination has been described in the literature (see, for example, Tang et al. (1992) *Nature* 356: 152-154). Gold microprojectiles are coated with the vaccine cassette, then bombarded into skin cells.

The genetic vaccines are formulated according to the mode of administration to be used. One having ordinary skill in the art can readily formulate a genetic vaccine that comprises a genetic construct. In cases where intramuscular injection is the chosen mode of administration, an isotonic formulation is used. Generally, additives for isotonicity can include sodium chloride, dextrose, mannitol, sorbitol and lactose. Isotonic solutions such as phosphate buffered saline are preferred. Stabilizers include gelatin and albumin.

According to the present invention, prior to or contemporaneously with administration of the genetic construct, cells may be administered a cell stimulating or cell proliferative agent, which terms are used interchangeably and refer to compounds that stimulate cell division and facilitate DNA and RNA uptake.

Bupivacaine or compounds having a functional similarity may be administered prior to or contemporaneously with the vaccine. Bupivacaine is a homologue of mepivacaine and related to lidocaine. It renders muscle tissue voltage sensitive to sodium challenge and effects ion concentration within the cells. In addition to bupivacaine, mepivacaine, lidocaine and other similarly acting compounds, other contemplated cell stimulating agents include lectins, growth factors, cytokines and lymphokines such as platelet derived growth factor (PDGF), gCSF, gMCSF, epidermal growth factor (EGF) and IL-4. About 50 µl to about 2 ml of 0.5% bupivacaine-HCl and 0.1% methylparaben in an isotonic pharmaceutical carrier may be administered to the site where the vaccine is to be administered, preferably, 50 .mu.l to about 1500 µl, more preferably about 1 ml. The genetic vaccine may also be combined with collagen as an emulsion and delivered intraperatonally. The collagen emulsion provides a means for sustained release of DNA. 50 µl to 2 ml of collagen are used.

The efficiency of DNA vaccination may be improved by injection of cardiotoxin into the tissue about one week prior to the vaccination, as described by Davis et al. (1993) *FEBS Lett.* 333:146-150, and in the examples. The cardiotoxin stimulates muscle degeneration and regeneration. The muscle is injected with from about 0.1 to 10 µM of cardiotoxin dissolved in a pharmacologically acceptable vehicle.

The condition that is being treated, and the host immune status will determine the choice of autoantigen sequence(s). The host may be assessed for immune responsiveness to a candidate vaccine autoantigen by various methods known in the art.

The diagnosis may determine the level of reactivity, e.g. based on the number of reactive T cells found in a sample, as compared to a negative control from a naive host, or standardized to a data curve obtained from one or more patients. In addition to detecting the qualitative and quantitative presence of auto-antigen reactive T cells, the T cells may be typed as to the expression of cytokines known to increase or suppress inflammatory responses. It may also be desirable to type the epitopic specificity of the reactive T cells.

T cells may be isolated from patient peripheral blood, lymph nodes, or preferably from the site inflammation. Reactivity assays may be performed on primary T cells, or the cells may be fused to generate hybridomas. Such reactive T cells may also be used for further analysis of disease progression, by monitoring their in situ location, T cell receptor utilization, etc. Assays for monitoring T cell responsiveness are known in the art, and include proliferation assays and cytokine release assays.

Proliferation assays measure the level of T cell proliferation in response to a specific antigen, and are widely used in the art. In an exemplary assay, patient lymph node, blood or spleen cells are obtained. A suspension of from about $10^4$ to $10^7$ cells, usually from about $10^5$ to $10^6$ cells is prepared and washed, then cultured in the presence of a control antigen, and test antigens. The test antigens may be peptides of any autologous antigens suspected of inducing an inflammatory T cell response. The cells are usually cultured for several days. Antigen-induced proliferation is assessed by the monitoring the synthesis of DNA by the cultures, e.g. incorporation of $^3$H-thymidine during the last 18 H of culture.

Enzyme linked immunosorbent assay (ELISA) assays are used to determine the cytokine profile of reactive T cells, and may be used to monitor for the expression of such cytokines as IL-2, IL-4, IL-5, γIFN, etc. The capture antibodies may be any antibody specific for a cytokine of interest, where supernatants from the T cell proliferation assays, as described above, are conveniently used as a source of antigen. After blocking and washing, labeled detector antibodies are added, and the concentrations of protein present determined as a function of the label that is bound.

The above diagnostic assays may be performed with various peptides derived from the autologous protein of interest. A series of peptides having the sequence of an auto-antigen, e.g. PLP, MBP, etc. may be used. Possible peptides may be screened to determine which are immunodominant in the context of autoimmune disease.

The immunodominant peptides may be defined by screening with a panel of peptides derived from the test protein. The peptides have the amino acid sequence of a portion of the protein, usually at least about 8 and not more than about 30 amino acids, more usually not more than about 20 amino acids in length. The panel of peptides will represent the length of the protein sequence, i.e. all residues are present in at least one peptide. Preferably overlapping peptides are generated, where each peptide is frameshifted from 1 to 5 amino acids, thereby generating a more complete set of epitopes. The peptides may be initially screened in pools, and later screened for the exact epitope to which the T cell will respond, as previously described. Immunodominant peptides are recognized by a significant fraction of the HLA restricted, responsive hybridomas, usually at least about 10%, more usually at least about 25%, and may be as much as 80%.

The subject therapy will desirably be administered during the presymptomatic or preclinical stage of the disease, and in some cases during the symptomatic stage of the disease. Early treatment is preferable, in order to prevent the loss of function associated with inflammatory tissue damage. The presymptomatic, or preclinical stage will be defined as that period not later than when there is T cell involvement at the site of disease, e.g. islets of Langerhans, synovial tissue, thyroid gland, etc., but the loss of function is not yet severe enough to produce the clinical symptoms indicative of overt disease. T cell involvement may be evidenced by the presence of elevated numbers of T cells at the site of disease, the presence of T cells specific for autoantigens, the release of performs and granzymes at the site of disease, response to immunosuppressive therapy, etc.

Degenerative joint diseases may be inflammatory, as with seronegative spondylarthropathies, e.g. ankylosing spondylitis and reactive arthritis; rheumatoid arthritis; gout; and systemic lupus erythematosus. The degenerative joint diseases have a common feature, in that the cartilage of the joint is eroded, eventually exposing the bone surface. Destruction of cartilage begins with the degradation of proteoglycan, mediated by enzymes such as stromelysin and collagenase, resulting in the loss of the ability to resist compressive stress. Alterations in the expression of adhesion molecules, such as CD44 (Swissprot P22511), ICAM-1 (Swissprot P05362), and extracellular matrix protein, such as fibronectin and tenascin, follow. Eventually fibrous collagens are attacked by metalloproteases, and when the collagenous microskeleton is lost, repair by regeneration is impossible.

There is significant immunological activity within the synovium during the course of inflammatory arthritis. While treatment during early stages is desirable, the adverse symptoms of the disease may be at least partially alleviated by treatment during later stages. Clinical indices for the severity of arthritis include pain, swelling, fatigue and morning stiffness, and may be quantitatively monitored by Pannus criteria. Disease progression in animal models may be followed by measurement of affected joint inflammation. Therapy for inflammatory arthritis may combine the subject treatment with conventional NSAID treatment. Generally, the subject treatment will not be combined with such disease modifying drugs as cyclosporin A, methotrexate, and the like.

A quantitative increase in myelin autoreactive T cells with the capacity to secrete IFN-gamma is associated with the pathogenesis of MS and EAE, suggesting that autoimmune inducer/helper T lymphocytes in the peripheral blood of MS patients may initiate and/or regulate the demyelination process in patients with MS. The overt disease is associated with muscle weakness, loss of abdominal reflexes, visual defects and paresthesias. During the presymptomatic period there is infiltration of leukocytes into the cerebrospinal fluid, inflammation and demyelination. Family histories and the presence of the HLA haplotype DRB1*1501, DQA1*0102, DQB1*0602 are indicative of a susceptibility to the disease. Markers that may be monitored for disease progression are the presence of antibodies in the cerebrospinal fluid, "evoked potentials" seen by electroencephalography in the visual cortex and brainstem, and the presence of spinal cord defects by MRI or computerized tomography. Treatment during the early stages of the disease will slow down or arrest the further loss of neural function.

Human insulin-dependent diabetes mellitus (IDDM) is a disease characterized by autoimmune destruction of the β cells in the pancreatic islets of Langerhans. An animal model for the disease is the non-obese diabetic (NOD) mouse, which develops autoimmunity. NOD mice spontaneously develop inflammation of the islets and destruction of the β cells, which leads to hyperglycemia and overt diabetes. Both CD4$^+$ and CD8$^+$ T cells are required for diabetes to develop: CD4$^+$ T cells appear to be required for initiation of insulitis, cytokine-mediated destruction of β cells, and probably for activation of CD8$^+$ T cells. The CD8$^+$ T cells in turn mediate β cell destruction by cytotoxic effects such as release of granzymes, perforin, TNFα and IFNγ. Reactivities to several candidate autoantigens, including epitopes of insulin and glutamic acid decarboxylase (GAD), have been detected.

In one embodiment of the invention, the coding sequence used for vaccination provides for an immunogenic insulin epitope. Immunodominant epitopes include the B chain, in particular residues 9-23, which have been implicated in both human disease and in animal models. Epitopes of the preproinsulin have also been implicated as immunodominant epitopes. Protection from diabetes is associated with down regulation of IFN-γ and IL-10 in pancreatic lymph node cells in response to the insulin peptide encoded in the vaccine. It has been found that T cells immunized with an immunodominant insulin epitope express substantially lower levels of IFN-γ in response to activation.

The depletion of β cells results in an inability to regulate levels of glucose in the blood. Overt diabetes occurs when the level of glucose in the blood rises above a specific level, usually about 250 mg/dl. In humans a long presymptomatic period precedes the onset of diabetes. During this period there is a gradual loss of pancreatic β cell function. The disease progression may be monitored in individuals diagnosed by family history and genetic analysis as being susceptible. The most important genetic effect is seen with genes of the major histocompatibility locus (IDDM1), although other loci, including the insulin gene region (IDDM2) also show linkage to the disease (see Davies et al, supra and Kennedy et al. (1995) *Nature Genetics* 9:293-298).

Markers that may be evaluated during the presymptomatic stage are the presence of insulitis in the pancreas, the level and frequency of islet cell antibodies, islet cell surface antibodies, aberrant expression of Class II MHC molecules on pancreatic β cells, glucose concentration in the blood, and the plasma concentration of insulin. An increase in the number of T lymphocytes in the pancreas, islet cell antibodies and blood glucose is indicative of the disease, as is a decrease in insulin concentration. After the onset of overt diabetes, patients with residual b cell function, evidenced by the plasma persistence of insulin C-peptide, may also benefit from the subject treatment, to prevent further loss of function.

Mammalian species susceptible to inflammatory conditions include canines and felines; equines; bovines; ovines; etc. and primates, particularly humans. Animal models, particularly small mammals, e.g. murine, lagomorpha, etc. may be used for experimental investigations. Animal models of interest include those involved with the production of antibodies having isotypes associated with IL-4 production, e.g. IgE, IgG1 and IgG4. Other uses include investigations where it is desirable to investigate a specific effect in the absence of T cell mediated inflammation.

It is to be understood that this invention is not limited to the particular methodology, protocols, formulations and reagents described, as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "a complex" includes a plurality of such complexes and reference to "the formulation" includes reference to one or more formulations and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the methods and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, and pressure is at or near atmospheric.

Experimental

Materials and Methods

Animals. Six to eight week old female SJL/J mice were purchased from Jackson Laboratory (Bar Harbor, Me.).

Antigens. Peptides were synthesized on a peptide synthesizer (model 9050: MilliGen, Burlington, Mass.) by standard 9-fluorenylmethoxycarbonyl chemistry. Peptides were purified by HPLC. Structure was confirmed by amino acid analysis and mass spectroscopy. Peptides used for the experiments were: PLP139-151 (SEQ ID NO:5 HSLGKWLGHPDKF), PLP139-151 L144/R147 (SEQ ID NO:6 HSLGKLLGRP-DKF), and PLP178-191 (SEQ ID NO:7 NTWTTCQSIAF-PSK). Guinea pig spinal cord homogenate (SCH) was used after lyophilization.

PLP peptide expression vector. Three minigenes, each one encoding a PLP epitope, were constructed by annealing two oligonucleotides with a 16 mer overlapping complementary sequence (underlined), and extending with DNA polymerase and dNTPs:

```
PLP (178-191):
5'-CTGGAGACCA GAATACCTGG ACCACCTGCC      SEQ ID NO:8
AGTCTATTGC CTTCCCTAGC AAGTCTAGAT AGCTA-3'

PLP (139-151):
5'-CTCGAGACCA TGCATTGTTT GGGAAAATGG      SEQ ID NO:9
CTAGGACATCCCGACAAGTTTTCTAGATAGCTA-3'.

PLP (139-151) L144/R147
5'-CTCGAGACCATGCATTGTTTGGGA              SEQ ID NO:10
AAACTACTAGGACGCCCCGACAAGTTTTCTAGATAGCTA-3'.
```

These oligonucleotide duplexes were designed to incorporate Xho I and Xba I restriction sites.

The products were cloned into the multiple cloning region of pTARGET Vector (Promega, Madison, Wis.), a mammalian expression vector driven by the CMV promoter. Positive clones were identified by color screening and correct orientation of the inserts was confirmed by DNA automatic sequencing. Purification of the plasmid DNA was done by Wizard plus Maxipreps (Promega) according to manufacturer instructions.

DNA immunization protocol. Experimental animals were injected in the left quadriceps with 0.1 ml of 0.25% bupivacaine-HCl (Sigma, St. Louis, Mo.) in PBS. Two and ten days later, mice were injected with 0.05 ml of plasmid DNA (1 mg/ml in PBS), in the same muscle.

ELISA for anti-PLP139-151 or anti-guinea pig SCH antibody titers. Polystyrene 96 well microtiter plates (Dynatech, Chantilly, Va.) were coated with 0.1 ml of either peptide or guinea pig SCH, diluted in PBS at a concentration of 0.01 mg/ml in PBS. After blocking with PBS+0.5% fetal calf serum (Gibco) and 0.05% tween 20 (Bio-Rad, Hercules, Calif.), mouse sera were incubated for two hours at room temperature and antibody binding was tested by the addition of alkaline phosphatase-conjugated goat anti-mouse IgG (Southern Biotechnology, Birmingham, Ala.). After the addition of the enzyme substrate, plates were read at 405 nm in an ELISA reader. FIG. 1 shows the results for sera taken seven days after the second intramuscular injection expressed as O.D. of individual samples in a group of ten animals. O.D. values for preimmune sera were: dilution 1:10:0.12, dilution 1:20:0.08, and dilution 1:40:0.03.

EAE induction. PLP139-151 peptide was dissolved in PBS to a concentration of 2 mg/ml and emulsified with an equal volume of Incomplete Freund's Adjuvant supplemented with 4 mg/ml heat-killed mycobacterium tuberculosis H37Ra (Difco Laboratories, Detroit, Mich.). Mice were injected subcutaneously with 0.1 ml of the peptide emulsion and, on the same day and 48 h later, intravenously with 0.1 ml of 4 µg/ml Bordetella Pertussis toxin in PBS. Experimental animals were scored as follows: 0=no clinical disease; 1=tail weakness or paralysis; 2=hind limb weakness; 3=hind limb paralysis; 4=forelimb weakness or paralysis; 5=moribund or dead animal.

Figure 2:
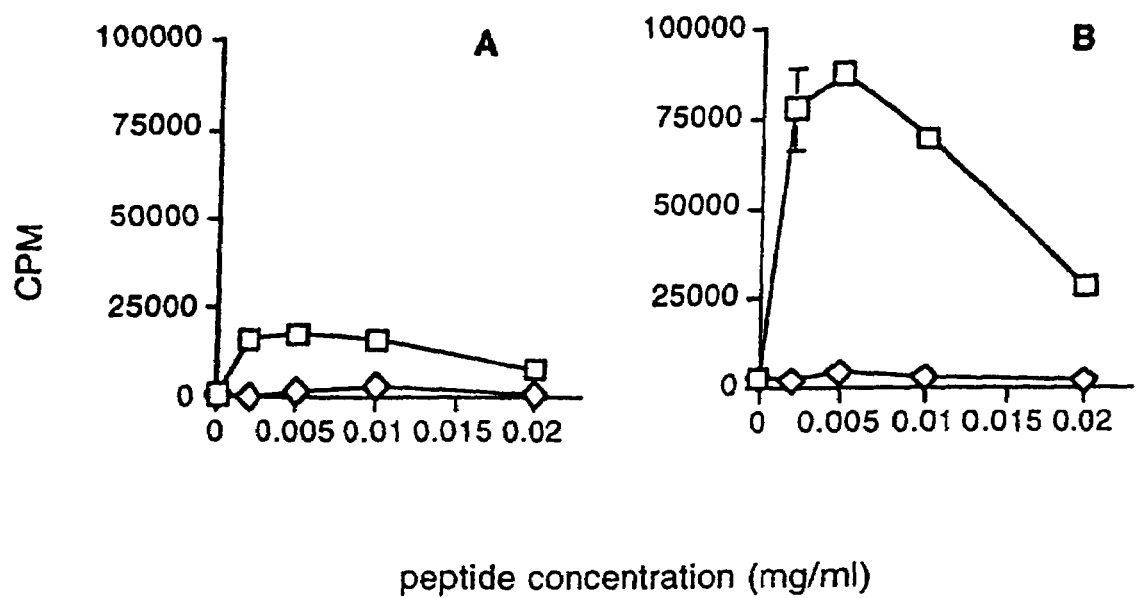
FIG. 2. Lymph node cell proliferative responses to PLP139-151 (squares) and the control peptide PLP178-191 (triangles) for animals injected with DNA coding for PLP139-151 (A) or control vector, pTARGET (B).

Lymph node cell proliferation assays. Draining lymph nodes were removed from mice after the acute phase of disease and lymph node cells (LNC) were tested in vitro for specific proliferative responses to the PLP139-151 peptide. Cultures were prepared in flat bottom 96 well microtiter plates in a volume of 0.2 ml/well at a cell concentration of 2.5×10⁶/ml. The tissue culture media for the assay consisted of RPMI 1640 supplemented with L-glutamine (2 mM), sodium pyruvate (1 mM), non essential amino acids (0.1 mM), penicillin (100 U/ml), streptomycin (0.1 mg/ml), 2-mercaptoethanol (5×10$^{-5}$ M), and 1% autologous fresh normal mouse serum. After 72 h of incubation at 37° C., cells were pulsed for 18 h with 1 µCi/well of (³H)thymidine. Plates were harvested and (³H)thymidine incorporation was measured in a scintillation counter. After recovery from the acute phase of disease animals injected either with DNA coding for PLP139-151 or control vector, pTARGET were sacrificed, and draining LNC were isolated. Cells were tested in vitro by stimulation with different concentrations of the peptide PLP139-151 or the control peptide PLP178-191. Proliferative responses from pooled LNC of groups of five animals are shown in FIG. 2 as mean CPM±SD of triplicate wells. CPM of Concanavalin A (0.001 mg/ml) stimulated LNC were 102401 for group A and 76702 for group B.

Cytokine determination. Draining LNC (10⁷ cells/ml) from experimental animals were taken after the acute phase of the disease and stimulated in vitro with varying concentrations of antigen. After 24 and 48 h of stimulation supernatants were collected and tested by sandwich ELISA.

Ribonuclease protection assay. For mRNA detection tissue RNA samples of LNC from experimental animals were tested using the Multi-Probe RNase Protection Assay (RPA) System, RiboQuant (Pharmigen, San Diego, Calif.) according to manufacturer instructions.

Figure 4:
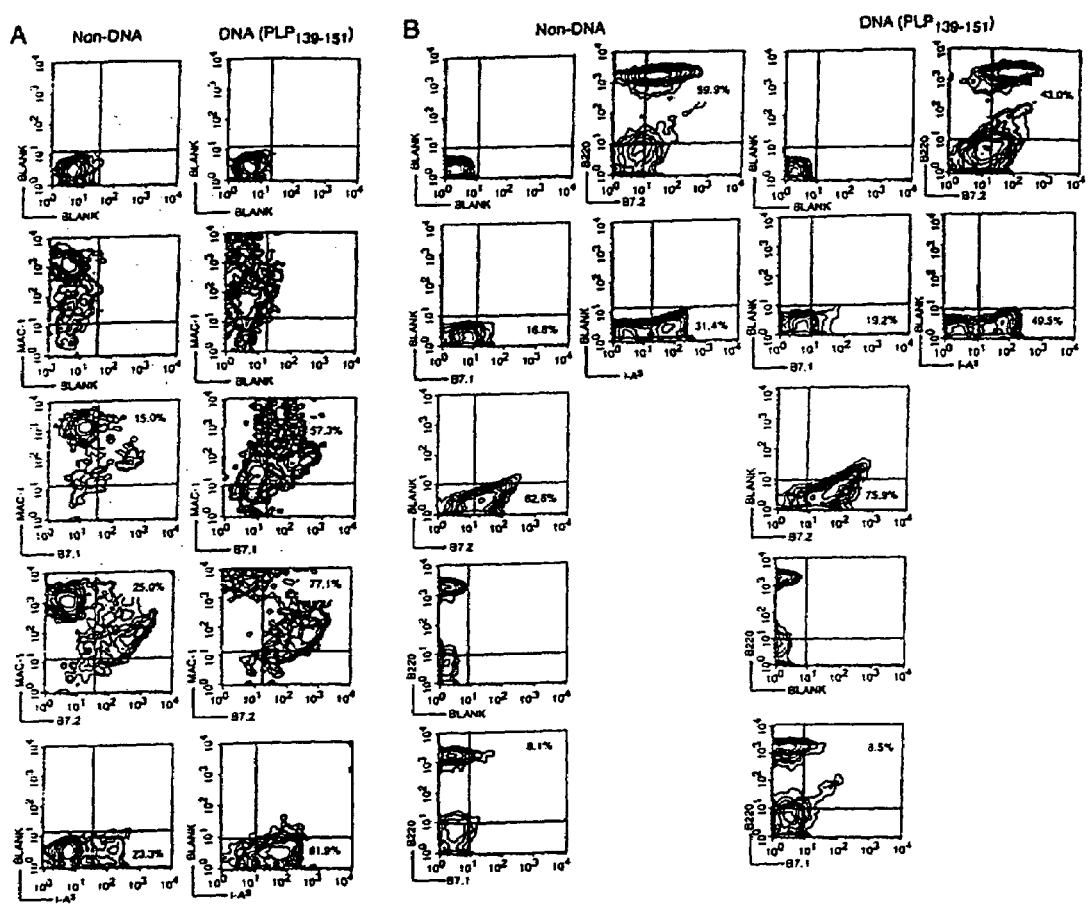
FIG. 4. Surface expression of B7.1, B7.2, and I-A$^s$ of spleen cells after incubation with DNA. Numbers in quadrants refer to the percentage of cells in the monocyte gate (A) or the lymphocyte gate (B) as defined by forward and side scatter.

Fluorocytometric analysis. Spleen cells (5×10⁶/ml) from naive SJL/J mice were incubated in the presence of plasmid DNA coding for the PLP139-151 sequence (0.01 mg/ml) at 37°C. After 24 h cells were collected and analyzed on FAC-Scan flow cytometer (Becton Dickinson). The following antibody conjugates were used: FITC anti-mouse CD80, clone 16-10A1; FITC anti-mouse CD86, clone GL1; FITC anti-mouse I-A$^k$, clone 10-3.6; R-PE conjugated anti-mouse B220, clone RA3-6B2; R-PE conjugated anti-mouse CD11b, clone M1/70; PE conjugated anti-mouse, clone GK 1.5. All antibodies were purchased from Pharmigen, San Diego, Calif. After 24 h of in vitro incubation without DNA (non) or with plasmid DNA coding for the PLP139-151 peptide [DNA (PLP139-151)], spleen cells were stained with anti-Mac 1 mAb, anti-B220 mAb, anti-B7.1 mAb, and anti-B7.2 mAb as indicated. Blank refers to nonspecific background staining. Results shown in FIG. 4 are representative of three experiments.

Results

The minigene, coding for the PLP139-151 peptide, was cloned into an expression vector and injected intramuscularly into SJL/J mice, twice, at one week intervals. Ten days after the last injection, experimental animals were bled and their sera were tested for the presence of specific antibodies. As shown in FIG. 1, anti-PLP139-151 IgG titers can be detected in the mice previously injected with the PLP139-151 minigene. Thus, specific serological immune responses are induced with this particular construct.

To determine whether injection of DNA containing PLP sequences can be effective in protecting mice from EAE induction, the PLP139-151 minigene construct was injected, intramuscularly, twice, at one week intervals. Ten days after the last injection, mice were challenged with the PLP139-151 peptide emulsified in CFA. As shown in Table 1, amelioration of acute clinical disease is observed in the animals vaccinated with the PLP139-151 plasmid vector, as compared with the control plasmid group. Onset of disease was delayed compared to the control plasmid group (11.5±0.5 days, p<0.008), mean peak disease severity was reduced (p<0.005), and mean disease score was reduced (p<0.0005). In addition, other groups were injected with either a) a plasmid containing a minigene encoding the altered peptide ligand PLP p139-151 (W144>L, H147>R), b) a plasmid containing a minigene encoding the PLP epitope p178-191. Onset of disease was delayed (11.6±0.5 days, p<0.009) and mean peak disease score was reduced (p<0.02) with the minigene encoding the altered peptide ligand (W144, H147). Also, onset of disease was delayed (11.5±0.4 days, p<0.003), mean peak disease severity was reduced (p<0.007), and mean disease score was reduced (p<0.0001) with the minigene encoding the PLP peptide p178-191.

TABLE 1

EAE induction in DNA immunized SJL/J mice.

| DNA injected | Percent incidence | Mean disease score on day 11† | Mean day of disease onset | Mean peak disease severity |
|---|---|---|---|---|
| PLP 139-151 | 68 (13/19)* | 0.9 ± 0.3 (p < 0.0005)¶ | 11.5 ± 0.5 (p < 0.008) | 1.7 ± 0.4 (p < 0.005) |
| PLP 178-191 | 70 (14/20) | 0.6 ± 0.2 (p < 0.0001) | 11.5 ± 0.4 (p < 0.0035) | 1.8 ± 0.3 (p < 0.007) |
| PLP 139-151 (L > R) | 85 (17/20) | 1.2 ± 0.3 (p < 0.001) | 11.6 ± 0.5 (p < 0.009) | 2.0 ± 0.3 (p < 0.01) |
| pTARGET | 90 (18/20) | 2.7 ± 0.3 | 10.1 ± 0.27 | 3.1 ± 0.3 |
| Non-plasmid | 100 (10/10) | 2.1 ± 0.7 | 9.9 ± 0.4 | 3.3 ± 0.3 |

*Numbers in parenthesis denotes sick animals over tested animals
†Means given as mean ± SEM.
¶All p values given as comparison to pTARGET by student's t-test.

Figure 3:
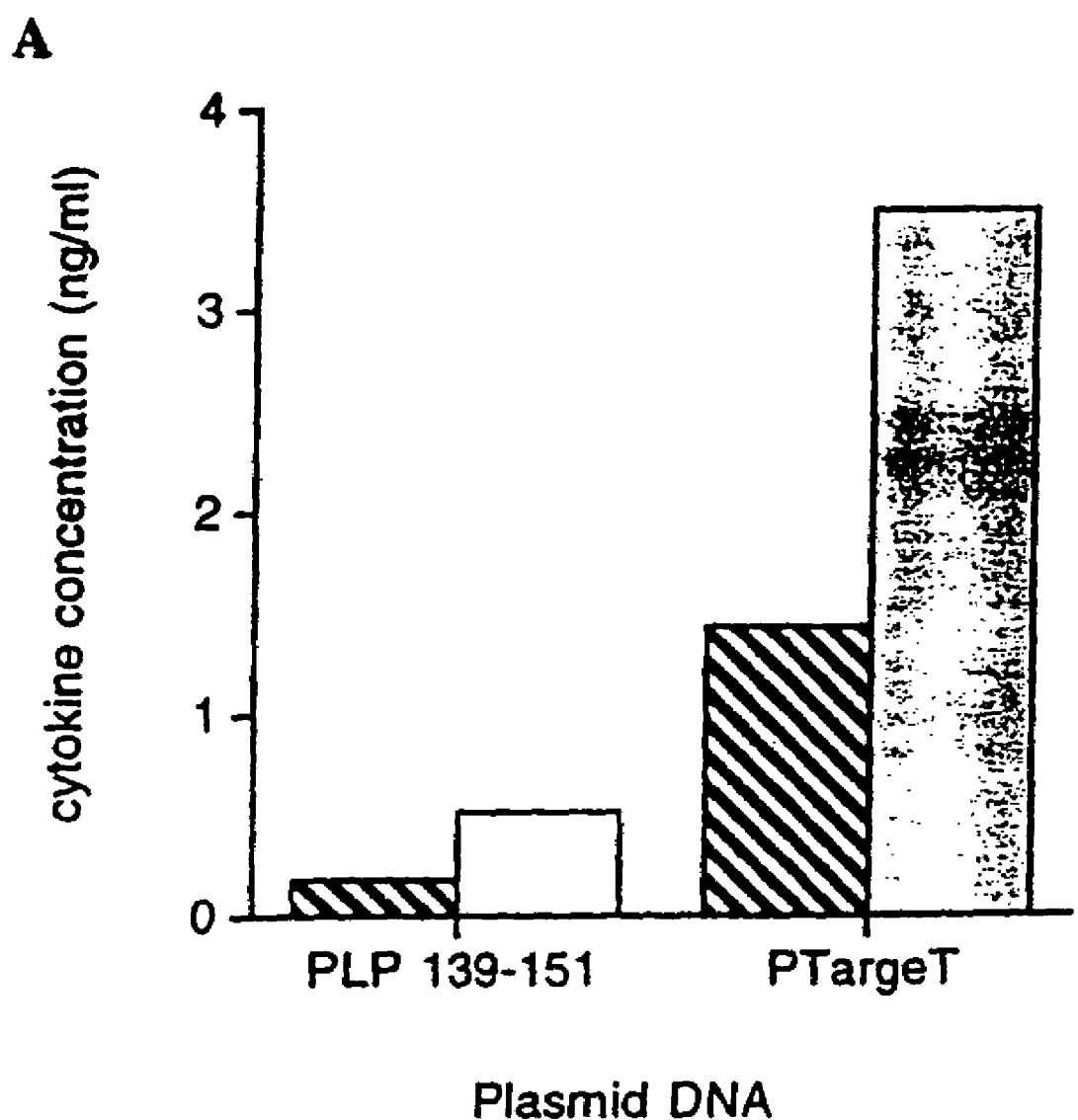
FIG. 3. (A) Levels of γ-interferon (striped bars) or IL-2 (dotted bars) in animals vaccinated with plasmid DNA coding for PLP139-151 or vector alone (pTARGET). (B) Cytokine mRNA detection and analysis by 5% polyacrylamide gel electrophoresis.
Figure 3B:
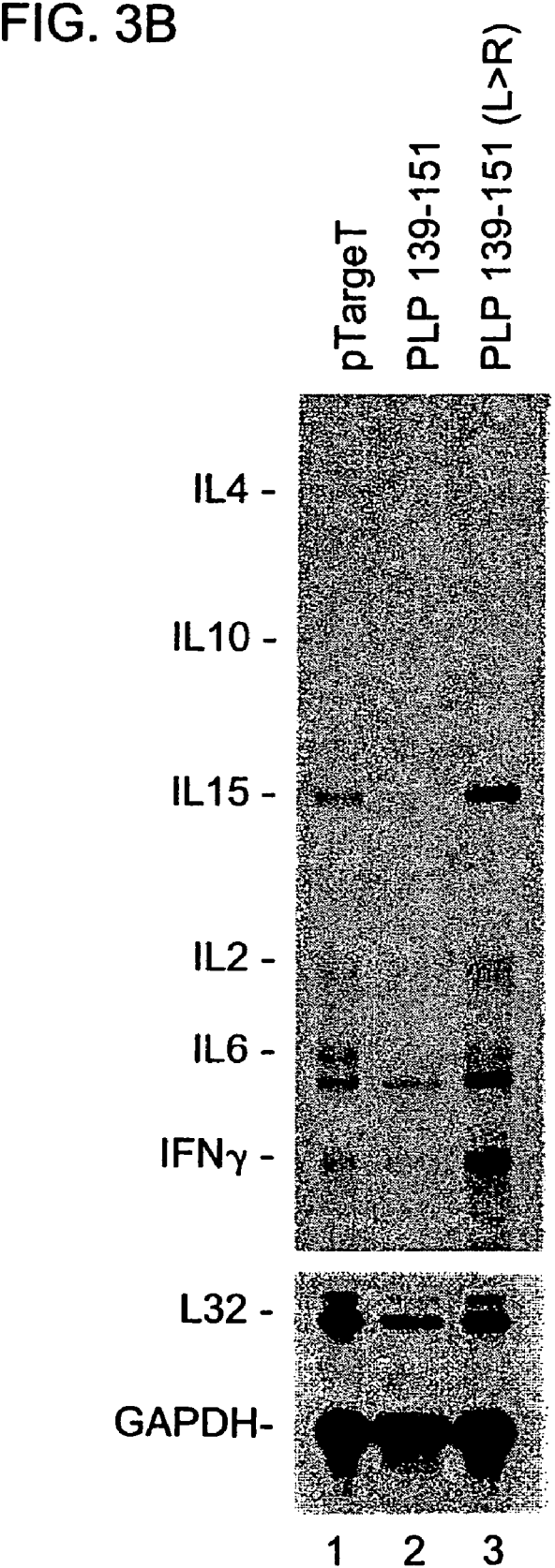

Mice, injected with DNA and further challenged with the encephalitogenic peptide PLP139-151, were sacrificed after resolution of the acute phase of the clinical disease. Draining LNC were restimulated in vitro with the PLP139-151 peptide and tested for their proliferative responses and cytokine production. FIG. 2 shows that LNC from mice injected with DNA coding for the PLP139-151 peptide had lower proliferative responses when compared with the LNC from control animals (p<0.01). FIG. 3 (A) shows that, when stimulated with the PLP139-151, LNC from mice immunized with the plasmid DNA coding for the PLP139-151 region secrete lower levels of IL-2 and γ-interferon in comparison with control groups. In order to assess levels of cytokine mRNA transcripts in inflamed brain we utilized a ribonuclease protection assay on mRNA isolated from brain tissue. FIG. 3 (B) reveals a reduction in mRNA levels of γ-interferon and IL-15 in mice immunized with the minigene encoding the PLP139-151 region. Therefore, a correlation between low incidence of clinical disease, reduced cellular responses, and low levels of IL-2, IL-15 and γ-interferon is evident in the PLP139-151 DNA vaccinated mice. The relative expression levels of cytokine mRNA's bands shown in FIG. 3B were measured by densitometry. In order to correct for loading differences, the values were normalized according to the level of expression of the housekeeping gene, GAPDH, within each sample. There is a reduction of expression level of the tested cytokines in brains of mice vaccinated with the plasmid DNA coding for the PLP139-151 determinant compared to pTARGET and PLP139-151 (L/R) plasmid DNA vaccinated mice.

In order to elucidate a mechanism for decreased T cell responses, we tested in vitro the effect of APCs, cultured in the presence of DNA, on the proliferative responses of PLP139-151 specific T cells. Splenocytes were incubated either with plasmid DNA coding for the PLP139-151 segment, or with the PLP139-151 peptide and used as a source of APC to stimulate L139 cells, a PLP139-151 specific T cell line. Proliferative responses of the L139 T cell line to the above APCs were compared in the presence or absence of anti-CD28 antibody coated beads. As shown in Table 2, L139 cells responded to syngeneic APCs preincubated with the synthetic peptide PLP139-151 [8512 mean cpm]. This response is increased with addition of anti-CD28 antibodies [127281 mean cpm]. However, when the APCs were incubated with the plasmid DNA containing PLP139-151 coding sequence, L139 cells were unable to respond to APCs [3358 mean cpm], even in the presence of anti-CD28 antibodies [4532 mean cpm]. This downregulation was not an effect of the plasmid itself, since APCs incubated with plasmid containing an irrelevant sequence did not affect the proliferative response of L139 cells to anti-CD28 antibodies [4532 cpm versus 26363 mean cpm, p<0.0001]. Therefore, PLP139-151 specific T cells are unable to respond to CD28 co-stimulation when cultured in the presence of APC loaded with plasmid DNA coding for the PLP139-151 sequence.

TABLE 2

Proliferative responses of PLP139-151 specific T cells line in the presence of syngeneic splenocytes loaded with either plasmid DNA or synthetic peptide.

| pTARGET plasmid DNA[1] | PLP139-151 plasmid DNA[1] | HSV-VP16 peptide[1] | PLP139-151 peptide[1] | Anti-CD28 co-stimulation[2] | CPM[3] (mean) |
|---|---|---|---|---|---|
| − | − | − | − | − | 2186 |
| − | − | + | − | − | 2402 |
| − | − | + | − | + | 15139 |
| − | − | − | + | − | 8512 |
| − | − | − | + | + | 127281 |
| + | − | − | − | − | 2331 |
| + | − | − | − | + | 26363* |
| − | + | − | − | − | 3358 |
| − | + | − | − | + | 4532* |

[1]Splenocytes (5 × 10[6]/ml)from naive SJL/J mice were irradiated (3000 rads) and incubated in the presence of either plasmid DNA coding for the PLP139-151 sequence, plasmid alone (pTARGET), PLP139-151 peptide, or control peptide (HSV VP16). Plasmid DNA concentration was 0.01 mg/ml and peptide concentration was 0.001 mg/ml. After the initial 24 hrs of incubation splenocytes were washed twice and 10,000 T cells from the PLP139-151 peptide-specific T cell line, L139, were added to each well. After 48 hrs of further incubation plate was labeled with $^3$H-thymidine and proliferation was assessed by harvesting 18 later and counting $^3$H-thymidine incorporation. To demonstrate that the exogenously applied naked DNA is taken up by the splenocytes, and is expressed we used reverse transcriptase-polymerase chain reaction (RT-PCR) technique. Total RNA was purified from the splenocytes using the Rneasy total RNA kit (Quiagen Inc., Valencia, CA). RT-PCR was performed using the Access RT-PCR System (Promega Corp., Madison, WI) and oligonucleotide primers specific for the PLP139-151 minigene. Vector specific primers were used in a separate RT-PCR reaction to exclude the possibility of DNA contamination. A single band corresponding to the PLP139-151 minigene was amplified from total RNA purified from splenocytes loaded with the PLP139-151 plasmid DNA (data not shown).
[2]Co-stimulatory signal was delivered by adding anti-CD28 coated beads (5,000 per well) together with the T cells. Anti-CD28 antibody (clone 37.51) was obtained from PharMingen (San Diego, CA). Sulfate polystyrene latex microspheres of ~0.1 µm in diameter were obtained from Interfacial Dynamics Corporation (Portland, OR). Beads (6 × 10[6]) were suspended in 6 ml of PBS and incubated with 24 µg of anti-CD28 antibody for 1.5 hours at 37° C. Beads were washed extensively with PBS and resuspended in RPMI-10% FCS and allowed to block for at least 30 minutes at room temperature.
[3]Results are expressed as mean CPM of triplicate wells.
*The P value is <0.0001 for the difference between the CPM of T cells incubated in the presence of splenocytes with pTARGET plasmid DNA versus T cells incubated in the presence of splenocytes with PLP139-151 plasmid DNA, in the presence of anti-CD28 antibodies.

The present study demonstrates protection from immunization with plasmid DNA encoding myelin minigenes. A DNA vaccine was created by insertion of the coding sequence for the PLP139-151 region into a bacterial plasmid under the control of CMV promoter. This vector was injected into SJL/J mice prior to the induction of EAE by immunization with the PLP139-151 peptide in CFA. Animals receiving the plasmid coding for the encephalitogenic epitope were protected from EAE induction. Analysis of the immune responses in protected animals demonstrates lower T cell proliferation and decreased pro-inflammatory cytokine secretion, both in lymphoid organs and within the target organ, the brain, in comparison with the control group. These features suggest that DNA immunization anergizes pathogenic T cells.

The ability of myelin minigene constructs to downregulate the co-stimulatory effect of anti-CD28 antibodies on a PLP-specific T cell line emphasizes its capacity to modulate APC-T cell interactions. Fluorocytometric analyses were carried out to determine whether DNA immunization influences the surface expression of CD28 ligands on APCs. After 24 h of incubation with the plasmid DNA, splenocytes were stained with either anti-B7.1 (CD80) or anti-B7.2 (CD86) antibodies. As shown in FIG. 4, up regulation of B7.1 and B7.2 is observed in Mac-1 positive cells, but not in B220$^+$ cells where downregulation of B7.2 was observed. I-A$^s$ expression in spleen cells also increased in both Mac-1 and B220 positive cells. upon incubation with DNA.

Similar up-regulation of costimulatory molecules has been observed in vivo in peripheral blood lymphocytes and spleen cells of animals inoculated with DNA expression cassettes coding for the HIV core protein 55. In contrast to this observation we found that in autoimmune responses to PLP139-151 the changes of expression of co-stimulatory molecules after DNA immunization exert a protective effect by modulation of the proliferative potential and cytokine production of autoreactive T-cells. Recently it has been reported that in EAE, there is enhancement of B7.1 expression relative to B7.2 in the splenic environment, a finding that can help explain how the immune system tilts toward autoimmunity, rather than immunological ignorance of self. Interestingly B7.2 increases in the CNS during active EAE and during relapses. Downregulation of B7.2 correlates with remission. Changes in B7-1 and B7-2 expression upon uptake of DNA by antigen presenting cells could be a key factor in regulating T-cell responses toward self-antigens in autoimmune diseases.

DNA vaccines have been effective in generating protective immune responses in several models of cancer, and of viral, bacterial, and parasitic infections. Although generation of Th1-like responses may be a property of DNA vaccines targeting non-self antigens, Th1 responses elicited to self with DNA vaccination have not been achieved.

Biological effects of DNA motifs like unmethylated CpG dinucleotides in particular base contexts (CpG-S motifs) may modulate innate immune responses when injected to animals (Krieg, A. M. et al. 1998. Trends in Microbiol. 6, 23-27). Although we cannot discard a possible effect of such sequences in the PLP 139-151 and PLP 139/151 (UR) constructs, the CG motifs in these inserts do not fulfill the complete criteria for a CpG-S motif.

Suppression of EAE has been reported in Lewis rats by previous immunization with DNA encoding an immunodominant MBP peptide in tandem with IgG Fc receptor. Vaccination suppressed clinical and histopathological signs of EAE, and reduced the interferon γ production after challenge with MBP 68-85 peptide [Lobell et al. (1998) J. Exp. Med. 187:1543-1548]. Vaccination was unsuccessful without inclusion of the tandem IgG Fc construct. In the experiments presented here, there was apparently no need for any tandem construct in conjunction with the myelin minigene. In both the present paper and in the experiments utilizing DNA with the Fc IgG construct, defective Th1 immunity to self was observed. In contrast, our laboratory has reported induction of protective Th2-type responses by DNA immunization in EAE [Waisman, 1996 supra.]. Therefore, the immune response to a DNA vaccine encoding self might be very different from what is observed with DNA vaccination to foreign antigens. It might be predicted that immune responses induced by self antigens encoded in DNA vaccines will parallel what has been observed for immunization with the same self-antigen in peptide or protein form. Our results suggest that a self antigen encoded in a DNA vector can anergize self-reactive T cells, and prevent an autoimmune attack. Co-stimulation of T cells by DNA encoding self-antigens is impaired, thus attenuating pathogenic T-cells. Our observations in the EAE suggest a model where DNA immunization can be utilized for treatment of autoimmune disease.

EXAMPLE 2

Protection Against Autoimmune Disease with an Interleukin-4 DNA Co-vaccine Via Induction of T-helper 2 Cells and STAT6 Activation The following example demonstrates that that co-vaccinating the genes for the cytokine IL4 along with the gene for PLP$_{139-151}$, as two separate plasmids can provide protective immunity against EAE. In addition, a mechanism is proposed, in which functional IL4 expressed from the DNA vaccine acts locally on autoreactive T cells via activation of STAT6 to shift their cytokine profile to a Th2 type. These results show the engineering of a novel method of treatment of autoimmune disease that combines the antigen specific effects of DNA vaccination along with the beneficial effects of local gene delivery.

Results

The IL4 DNA vaccine produces IL4 protein. In order to construct the IL4 DNA vaccine, the complete coding sequence for IL4 was amplified by PCR from mouse spleen cDNA. This gene was cloned into the mammalian expression vector pTargeT under control of the CMV promoter, and the plasmid was purified as described in the methods. In order to demonstrate that the IL4 cDNA construct can indeed produce full-length IL4 protein, an in vitro translation system was used. When the IL4 cDNA plasmid was transcribed and translated in vitro with $^{35}$S-methionine and resolved by SDS-PAGE (polyacrylamide gel electrophoresis) and autoradiography, a single product of the correct size for mouse IL4 was seen. A control reaction with vector DNA without insert or plasmid encoding PLP$_{139-151}$ produced no detectable product. The predicted molecular weight for PLP$_{139-151}$ is approximately 1.5 kD and, therefore, would be extremely difficult to visualize by electrophoresis.

IL4 DNA vaccination causes activation of STAT6. In order to demonstrate that a DNA vaccine can act as a gene delivery vehicle, we wanted to explore the question of whether functional IL4 cytokine was actually expressed from the DNA vaccine administered to the animal. IL4 is known to act through the IL4 receptor to specifically activate STAT6, a member of the signal transducers and activators of transcription family (Takeda et al. (1996) Nature 380:627-30; Quelle et al. (1995) Mol Cell Biol 15:333643.

Mice were vaccinated intramuscularly on a once weekly basis with plasmid DNA encoding the IL4 cDNA as described in the methods. Draining lymph nodes were dissected one week after the last DNA vaccine. Protein lysates were isolated from the lymph node cells, and probed for the presence of activated STAT6 by Western blotting using a polyclonal antibody specific for the phosphorylated form of STAT6. As controls, mice were also vaccinated with pTargeT vector alone or with no DNA. Activated or phosphorylated STAT6 was only seen in lymph nodes from IL4 DNA vaccinated mice. The phosphorylated STAT6 identified runs at approximately 60 kD.

Identical results were obtained in a separate experiment in which mice received three daily, rather than weekly, doses of the DNA vaccine. Mice were vaccinated intramuscularly with plasmid DNA on a daily basis for three days. One day after the last DNA vaccine, protein lysates from draining lymph nodes were obtained and analyzed as above in an anti-phosphorylated STAT6 Western. A 60 kD band was seen only in the lymph node cells from IL4 DNA vaccinated mice.

Co-vaccination with DNA encoding IL4 and the $PLP_{139-151}$ minigene protects against EAE induction. In order to explore the effect of modifying the protection afforded by DNA immunization with the gene encoding $PLP_{139-151}$, we co-vaccinated mice with the genes for IL4 and $PLP_{139-151}$ as two separate plasmids. The murine IL4 gene was cloned into the mammalian expression vector pTargeT under control of the CMV promoter as described earlier. The gene encoding $PLP_{139-151}$ was obtained as described above.

SJL/J mice were injected with 100 μg of each plasmid intramuscularly twice, at one-week intervals. Control mice were injected with vector alone or with PBS. Ten days after the last injection, the mice were challenged for induction of EAE with the encephalitogenic peptide $PLP_{139-151}$, emulsified in complete Freund's adjuvant (CFA). As shown in Table 3, there is a significant decrease in the mean disease scores of mice co-vaccinated with both the IL4 and $PLP_{139-151}$ plasmids compared to controls (see table for p values). There is also a decrease in the incidence of disease and mean peak disease severity with the co-vaccine compared to controls. The onset of disease was not significantly delayed compared to the control groups. No significant protection from disease was seen in mice vaccinated only with DNA encoding IL4.

Co-vaccination with DNA encoding IL4 changes the phenotype of T cells into a Th2 type. $PLP_{139-151}$ specific T cells lines were isolated and maintained in culture from mice challenged for disease induction with the peptide $PLP_{139-151}$ and previously vaccinated with various combinations of DNA. These T cell lines were tested for cytokine production after in vitro stimulation with the peptide $PLP_{139-151}$. T cells from mice co-vaccinated with IL4 and $PLP_{139-151}$ DNA produced significantly higher amounts of IL4 (mean of 716±237 pg/ml vs. 0.208±0.36 pg/ml from pTargeT vaccinated mice, p<0.0064) and IL10 (mean of 1073±221 pg/ml vs. 464±44 pg/ml from pTargeT vaccinated mice, p<0.0151) compared to T cells from control mice. In addition, T cells from the IL4 and $PLP_{139-151}$ DNA co-vaccinated mice produced lower amounts of IFNγ compared to control T cells (mean of 1389±108 pg/ml vs. 6689±85 pg/ml from pTargeT vaccinated mice, p<0.0001). Thus, T cells isolated from the co-vaccinated and protected mice produce more Th2 type cytokines compared to control T cells. As reported above, T cells from mice vaccinated with $PLP_{139-151}$ DNA alone had a reduced amount of IFNγ, but did not undergo a Th2 shift.

Protection from EAE in IL4 and $PLP_{139-151}$ co-DNA vaccinated mice can be transferred by T cells. The T cells derived from mice co-vaccinated with both IL4 DNA and $PLP_{139-151}$ DNA, which maintained proliferative capacity but underwent a Th2 shift, were then tested for the capacity to transfer protection. Mice were immunized with the encephalitogenic peptide $PLP_{139-151}$, emulsified in CFA, and eight days later 10 million T cells were injected intravenously into each mouse.

TABLE 2

EAE disease severity in DNA vaccinated mice

| DNA | n | Percent Incidence | Mean[a] Peak Disease Severity | Mean Score day 12 | Mean Score day 14 | Mean Score day 16 |
|---|---|---|---|---|---|---|
| None | 14 | 86 | 2.3 ± 0.3 | 1.6 ± 0.4 | 1.2 ± 0.2 | 0.7 ± 0.3 |
| pTargeT | 15 | 93 | 2.4 ± 0.2 | 1.6 ± 0.3 | 1.7 ± 0.2 | 1.1 ± 0.2 |
| IL4 | 15 | 80 | 2.7 ± 0.3 | 1.4 ± 0.3 | 1.1 ± 0.2 | 0.4 ± 0.2 |
| IL4 & PLP139-151 | 15 | 53 | 1.6 ± 0.3 | 0.8 ± 0.3 | 0.7 ± 0.3 | 0.5 ± 0.2 |
| | | (p < 0.0383)[b] | (p < 0.0494) | (p < 0.0075) | (p < 0.0411) |

[a]Means given as mean ± SEM.
[b]All p values given as comparison of IL4/PLP139-151 to pTargeT by Student's unpaired t test.

Co-vaccination with DNA encoding IL4 rescues the T cell proliferative responses in $PLP_{139-151}$ DNA vaccinated animals. Mice that were vaccinated with DNA and challenged for disease induction with peptide $PLP_{139-151}$ were sacrificed after recovery from the initial acute disease. Draining lymph node cells (LNC) were obtained from these mice and re-stimulated in vitro with the $PLP_{139-151}$ peptide to determine their proliferative responses. Furthermore, antigen specific T cell lines were maintained from these LNC in order to analyze their cytokine secretion profiles.

LNC were tested for their proliferative responses to the peptide $PLP_{139-151}$. There was no significant change in the proliferative pattern of LNC from IL4 and $PLP_{139-151}$ co-DNA vaccinated mice compared to control mice vaccinated with vector only. In contrast, LNC from mice vaccinated only with $PLP_{139-151}$ DNA have a reduced proliferative capacity. We have previously shown that these T cells are anergic (Example 1). Therefore, the addition of IL4 as a DNA co-vaccine is able to rescue the anergy imposed by the $PLP_{139-151}$ DNA vaccine. Thus, a different mechanism of protection may be afforded by co-vaccination with IL4 DNA compared with vaccination with $PLP_{139-151}$, DNA alone.

Animals were then followed for disease phenotype. Control T cells that are specific for $PLP_{139-151}$ and known to induce EAE were also injected as a control. Mice injected with T cells derived from the co-vaccinated mice had reduced incidence (1/5 mice compare to 4/5 mice in the controls) and reduced disease scores compared with control T cell injected mice. These results indicate that the protective effect achieved by IL4 and $PLP_{139-151}$ DNA co-vaccination can be transferred to naive animals by antigen specific Th2 cells.

Discussion

This example demonstrates a novel method of protective immunity which combines the effects of DNA vaccination and local gene delivery. First we demonstrated that the IL4 genetic vaccine delivers functional IL4. After confirming that full-length IL4 is indeed expressed in vitro from the DNA construct used for the vaccination, we then showed that STAT6 is activated in draining lymph node cells by the IL4 DNA vaccine. Because STAT6 is specifically activated by IL4, we believe that the most likely conclusion is that IL4 is produced from the DNA vaccine administered and that it interacts with IL4 receptor on lymph node cells, which in turn causes the activation of STAT6 downstream of the receptor. The phosphorylated STAT6 identified in the present study is approximately 60 kD. Although the predominant isoform of STAT6 described in the literature is 100 kD, other isoforms have been described in mouse immune tissues (Quelle et al., 1995). Furthermore, a recent study demonstrated the existence of a 65 kD isoform in mouse mast cells (Sherman et al., 1999). The IL4 delivered by the DNA genetic vaccine appears to specifically activate this isoform. We were not able to detect antibody responses against IL4 in the IL4 DNA vaccinated mice. Therefore, we postulate that the IL4 gene thus delivered and expressed is effective in generating protective immunity without induction of an immune response against IL4.

When mice were immunized with both the IL4 DNA vaccine and a separate DNA vaccine for the self-peptide $PLP_{139-151}$, these mice were protected against induction of disease by the peptide $PLP_{139-151}$, emulsified in CFA. The IL4 DNA vaccine alone did not provide significant protection. When the cytokine profile of T cells from co-vaccinated and protected mice were examined, a shift to a Th2 type of cytokine secretion pattern was seen. Furthermore, these Th2 cells could transfer protection against disease induction in naive mice. We thus propose that the combination of the local delivery of IL4 and vaccination with $PLP_{139-151}$ DNA causes the antigen specific autoreactive T cells to shift their phenotype to a more protective Th2 type of response. These antigen specific, protective T cells are then directed to sites of myelin damage and attenuate the pathogenic autoimmune response.

A possible mechanism as to how this phenotypic shift could occur is that the IL4 and the $PLP_{139-151}$ DNA vaccines are taken up by antigen presenting cells (APC's) at the site of administration of the vaccines. The $PLP_{139-151}$ peptide is expressed in the APC's and presented on MHC class II to antigen specific T cells that are thus recruited. The APC's also express IL4, which is secreted locally during the APC and T cell interaction. This secreted IL4 then causes the phenotype of the antigen specific T cell to assume a more Th2 type of phenotype. This model is compatible with earlier studies that showed that T cells grown in culture can be caused to assume a more Th2 type of phenotype by growth in the presence of IL4 (Macatonia et al. (1993) *Int Immunol* 5:1119-28).

Previous studies have demonstrated that professional APC's either present at the site of administration or recruited from the bone marrow can take up the naked DNA and travel to lymphoid organs (Chatterjoon et al. (1998) *J Immunol* 160:5707-18). It is possible that two separate or even distant APC's take up the two different plasmids. We believe, however, that it is the local microenvironment during the APC and T cell interaction that is important since no detectable increase in serum IL4 was seen in the IL4 DNA vaccinated mice. As a method of delivery of a potentially adverse gene product, such as a cytokine at high doses, this technique could be desirable over traditional gene therapy methods since the gene delivered acts locally rather than systemically.

DNA vaccines have proven to be effective in protecting against some animal models of autoimmune disease. One of the many advantages of DNA vaccines over traditional treatments of autoimmune disease is the ability to easily modify the treatment vehicle. We have shown here that with the addition of a genetically delivered IL4 cytokine to the $PLP_{139-151}$ DNA vaccine, we can protect against EAE and, further, drive the protective response to a more Th2 type. The addition of IL4 as a DNA co-vaccine rescues the anergy imposed by the $PLP_{139-151}$ DNA vaccine, and drives the response to a Th2 phenotype. This mechanism of protection afforded by co-vaccination with IL4 DNA compared with vaccination with $PLP_{139-151}$ DNA alone, may have particular advantages. This technique could prove beneficial in the treatment of other autoimmune diseases. Immunization against the antigens that trigger those autoimmune diseases caused by Th1 autoreactive cells, diseases such as multiple sclerosis, juvenile diabetes and rheumatoid arthritis, would be conditions where co-vaccination with DNA encoding IL-4 might prove beneficial. In conclusion, the data presented here imply a powerful and novel tool, namely the combination of local gene delivery and antigen specific DNA vaccination, that could be applied universally to all DNA vaccines.

Experimental Procedures

Animals. Six- to eight-week-old female SJL/J mice were purchased from The Jackson Laboratory (Bar Harbor, Me.).

Peptides. Peptides were synthesized on a peptide synthesizer (model 9050; MilliGen, Burlington, Mass.) by standard 9-fluorenylmethoxycarbonyl chemistry. Peptides were purified by HPLC. Structures were confirmed by amino acid analysis and mass spectroscopy. Peptides used in these experiments were: (SEQ ID NO:5) $PLP_{139-151}$ (HSLGK-WLGHPDKF) and (SEQ ID NO:15) HSVP16 P45(DMT-PADALDDRDLEM).

DNA vaccines. A minigene encoding $PLP_{139-151}$ was constructed as described above. The murine IL4 gene was cloned by PCR from spleen cDNA (Clontech, Palo Alto, Calif.) by use of the following PCR primers: (SEQ ID NO:16) 5'-CGCGGATCCTTGATGGGTCTCAAC-CCCCAGCTAGTTGTC-3' and (SEQ ID NO:17) 5'-ACGCTCGAGGTACTACGAGTAATC-CATTTGCATGATGC-3'. Both of these constructs were cloned into the multiple cloning region of the pTargeT vector (Promega, Madison, Wis.), driven by the CMV promoter. Correct clones were confirmed by automated DNA sequencing. Purification of the plasmid DNA was performed with the use of the Qiagen Endo-free Mega Prep kit (Qiagen, Santa Clarita, Calif.). Purity of the plasmid DNA was confirmed by UV spectrophotometry and agarose gel electrophoresis. Only DNA with a 260 nm/280 nm absorbance ratio of greater than 1.7 was used.

In vitro translation. DNA constructs used for DNA vaccination were tested for the production of the correctly sized product by an in vitro translation assay. Approximately 1 µg of plasmid DNA was incubated for 2 hours at 30° C. in a 50 µl volume containing the following: 25 µl of TNT rabbit reticulocyte lysate (Promega Corp., Madison, Wis.), 2 µl of TNT reaction buffer (Promega Corp., Madison, Wis.), 1 µl TNT T7 RNA polymerase (Promega Corp., Madison, Wis.), 1 µl of a 1 mM amino acid mixture minus methionine (Promega Corp., Madison, Wis.), 4 µl of $^{35}$S-methionine at 10 mCi/ml (Amersham Life Sciences Inc., Arlington Heights, Ill.), and 1 µl of RNasin ribonuclease inhibitor at 40 U/µl (Promega Corp., Madison, Wis.). A 3 µl volume of the products of this reaction was mixed with SDS-sample buffer and run on an 18% SDS polyacrylamide gel. After drying, the gel was then exposed to autoradiography film.

STAT6 Westerns. After dissection of draining lymph nodes from DNA vaccinated mice, the tissues were mechanically homogenized in 1 ml of the following buffer: 0.1 M NaCl, 0.01 M Tris-HCL pH7.4, 0.001 M EDTA, 1 µg/ml aprotinin, 1.6 µM Pefabloc SC (Boehringer Mannheim, Indianapolis, Ind.). 0.5 ml of the resultant lysate was used in a BCA protein assay (Pierce, Rockford, Ill.) in order to determine the total protein concentration. The remaining 0.5 ml was added to 0.25 ml of 3×SDS loading buffer (New England Biolabs, Beverly, Mass.) containing DTT at a final concentration of 0.04 M. The products were resolved on a 4-15% gradient SDS-PAGE gel (Bio-Rad, Hercules, Calif.). Prestained markers were used to determine the molecular weights (Bio Rad, Hercules, Calif.). After electrophoresis, the gels were blotted to PVDF membranes (Amersham Life Sciences Inc., Arlington Heights, Ill.) at constant voltage of 100 V in 25 mM Tris, 192 mM glycine and 20% (v/v) methanol as the transfer buffer. The membranes were blocked for 1 hour at room temperature with Tris buffered saline (TBS), 0.1% Tween 20, and 20% non-fat dry milk. After washing the membranes with TBS and 0.1% Tween 20, the membranes were hybridized overnight at 4° C. with anti-phospho STAT6 antibody (New England Biolabs, Beverly, Mass.) diluted 1:1000 in TBS, 0.1% Tween 20, 5% BSA. The membranes were then processed as in the ECL Plus protocol (Amersham Life Sciences Inc., Arlington Heights, Ill.) for visualization of the bands by chemiluminescence. The membranes were stripped by incubation in 100 mM β-mercaptoethanol, 2% (w/v) SDS, and 62.5 mM Tris-HCL pH 7.4 for 30 minutes at 60° C. These same membranes were then probed with an antibody against mouse CD3ζ (Pharmingen, San Diego, Calif.) as a control to verify equal loading of the lanes.

DNA immunization protocol. Animals were injected in the left quadriceps with 0.1 ml of 0.25% bupivicaine-HCL (Sigma, St. Louis, Mo.) in PBS. Two and 9 days later, mice were injected with 100 μg of plasmid DNA (at a concentration of 1 mg/ml in PBS) in the same muscle. Animals receiving a co-vaccine received two separate injections of each plasmid DNA.

EAE induction. Seven to 10 days after the final DNA vaccine, EAE was induced in mice with 100 μg of $PLP_{139-151}$ peptide. The peptide was dissolved in PBS at a concentration of 2 mg/ml and emulsified with an equal volume of incomplete Freund's adjuvant supplemented with 4 mg/ml heat killed mycobacterium tuberculosis H37Ra (Difco Laboratories, Detroit, Mich.). Mice were injected subcutaneously with 0.1 ml of the peptide emulsion. Experimental animals were scored as follows: 1, tail weakness or paralysis; 2, hind limb weakness; 3, hind limb paralysis; 4, forelimb weakness or paralysis; and 5, moribund or dead animals.

Lymph node cell proliferation assays. After the acute phase of disease, draining lymph nodes were dissected and lymph node cells (LNC) were cultured in vitro for specific proliferative response to the $PLP_{139-151}$ peptide. LNC's were prepared in 96-well microtiter plates in a volume of 0.2 ml/well at a concentration of $2.5 \times 10^6$ cells/ml. The culture medium consisted of enriched RPMI (RPMI 1640 supplemented with L-glutamine [2 mM], sodium pyruvate [1 mM], nonessential amino acids [0.1 mM], penicillin [100 U/ml], streptomycin [0.1 mg/ml], 2-ME [$5 \times 10^{-5}$ M]) supplemented with 1% autologous fresh normal mouse serum. Cultures were incubated at 37° C. and after 72 hours, cells were pulsed for 18 hours with 1 μCi/well of [$^3$H]thymidine. The cells were then harvested and counted in a beta counter.

Cytokine profile determination. T cell lines were established from LNC's derived from DNA vaccinated mice. These T cells were then tested for the production of various cytokines. $50 \times 10^3$ T cells/ml were incubated with $2.5 \times 10^6$ irradiated syngenic APC's/ml in enriched RPMI and 10% FCS. After 6 days of culture the supernatants were collected and tested by sandwich ELISA using standard ELISA kits (Pharmingen, San Diego, Calif.).

EXAMPLE 3

Immunization with DNA Encoding an Immunodominant Peptide of Insulin Prevents Diabetes in NOD Mice The NOD mouse is an animal model of IDDM in which several autoantigens, including insulin, have been identified. In this study it is proven that vaccination of NOD mice with DNA encoding an immunodominant peptide of insulin protects the animals from developing diabetes. These results confirm that DNA vaccination has a protective effect on autoimmunity and opens doors for novel therapies.

Materials and Methods

Animals. Three- to four-week-old female NOD mice were purchased from Taconic Farms (Germantown, N.Y.) and maintained in the Department of Comparative Medicine at Stanford University.

Mice were tested weekly for glucosuria by Chemstrip (Boehringer Mannheim Co., Indianapolis, Ind.), and diabetes was confirmed by plasma glucose measurement using the One Touch II meter (Johnson & Johnson, Milpitas, Ca). Animals having repeated plasma glucose levels greater than 250 mg/dl were considered diabetic.

Insulin peptide expression vectors. Overlapping sense and antisense oligonucleotide sequences encoding the A(7-21) and B(9-23) peptides of insulin were synthesized by the PAN facility at Stanford University Medical Center. The nucleotide sequence of the insulin A (+) strand is (SEQ ID NO:18) 5'CCGGAATTCGCCATGTGCACGTCAATCT-GTTCACTGTAC CAGCTAGAAACTACTGCAAC-TAGTCTAQGAGC-3'; the sequence of the insulin B (+) strand is (SEQ ID NO:19) 5'-CCGGAATTCGCCATGAGC-CACCTAGTAGAAGCACTAACC TCGTATGCGGC-GAACGAGGTTAGTCTAGAGC-3'. These were designed to incorporate EcoRI and XbaI restriction sites for cloning. The products were cloned into the multiple cloning region of PcDNA3.1$^+$ expression vector (Invitrogen, Carlsbad, Calif.). Purification of the plasmid DNA was carried out using Qiagen Endo-free Mega-prep kits (Qiagen, Valencia, Calif.).

Protein and peptides. Whole porcine insulin was purchased from Sigma (St. Louis, Mo.). Insulin peptides were synthesized and HPLC purified by the PAN facility at Stanford University. The amino acid sequence of the insulin A (7-21) peptide is (SEQ ID NO:20) CTSICSLYQLENYCN; the sequence of insulin B (9-23) is (SEQ ID NO:21) SHLVEALYLVCGERG. The control peptide "p43" is derived from *Bacillus subtilis* hyp protein X13 and has the sequence (SEQ ID NO:22) RKWTDFFKNIPQRI.

DNA Immunization Protocol. Experimental animals were injected at 3 to 4 weeks of age in the quadricep with 0.1 ml of 0.25% bupivicaine-HCL (Sigma, St. Louis, Mo.) in PBS (0.05 ml per quadricep). Two days following, mice were injected with 0.05 ml of plasmid DNA at 1.0 mg/ml in each quadricep. The plasmid DNA was injected two more times at ten-day intervals.

Histology. The pancreata were removed from experimental and control animals, fixed in 10% formaldehyde, and embedded in paraffin. Thin sections at three levels, 50 μm apart, were cut for staining with hematoxylin and eosin. The severity of infiltration was assessed by light microscopy. Three and five animals from each group were analyzed for two individual experiments, respectively. At least 25 islets were examined per pancreas.

Proliferation Assays. Ten days after the third injection of plasmid DNA, animals were sacrificed and their splenocytes tested in vitro for proliferative responses to insulin peptides and to other islet antigen peptides. A non-relevant peptide p43 was used as a control. Cells were plated in flat-bottom 96-well microtiter plates in a volume of 0.2 ml per well at a concentration of $2.5 \times 10^6$ cells per ml. Tissue culture media for the assay consisted of RPMI 1640 supplemented with L-glutamine (2 mM), sodium pyruvate (1 mM) nonessential amino acids (0.1 mM), penicillin (100 U/ml), streptomycin (0.1 mg/ml), 2-ME ($5 \times 10^{-5}$ M), and 1% autologous fresh normal mouse serum. After 72 hours of incubation at 37° C., cells were pulsed with 1 µCi/well of [$^3$H]thymidine for an additional 18 hours. Plates were harvested and [$^3$H] thymidine incorporation was measured in a scintillation counter.

Serum Antibody ELISAs. Polystyrene 96-well microtiter plates were coated with 100 µl peptide or protein at a concentration of 10 µg/ml in PBS. Plates were washed and blocked with PBS containing 5% FCS for 1 hour at room temperature. Diluted serum samples from vaccinated or non-treated animals was added and incubated overnight at 4° C. After washing, goat anti-mouse IgG conjugated to alkaline phosphatase (Southern Biotechnology Associates, Birmingham, Ala.) was added, and plates incubated for 1 hour at 37° C. After addition of the enzyme substrate, plates were read at 405 nm in an ELISA reader.

Real Time Quantitative PCR analysis of cytokine mRNA. Five days after the second injection, pancreatic lymph nodes were harvested and single cell suspension prepared. Ten million cells from each group were plated in 1.5 mL final volume with 10 µg/mL insulin B peptide. After 72 hours cells were collected and pelleted for RNA extraction using the RNeasy kit (Quiagen, Valencia, Calif.). The RNA was treated with DNase to remove all genomic DNA and reverse transcribed with MultiScribe reverse transcriptase (PE Applied Biosystems, Foster City, Calif.) in the presence of hexamers, according to manufacturer's instructions.

Real time quantitative PCR was carried out for IL-4, IFN-γ, IL-10, TGF-β, and ribosomal RNA (internal control) in the ABI Prism 7700 sequence detector, which contains a Gene-Amp PCR system R600 (PE Applied Biosystems). The probes were labeled with the fluorescent reporter dye FAM (6-carboxyfluorescein, covalently linked to the 5' end of the oligonucleotide) and a quencher, TAMRA. The primer and probe sequences used were the following: (SEQ ID NO:23) 5' IL-4 primer, CATCGGCATTTTGAA; (SEQ ID NO:24) 3' IL-4 primer, CGTTTGGCACATCCATCTCC; IL-4 probe, (SEQ ID NO:25) CACAGGAGAAGGGACGCCATGCA; 5' IFN-γ primer, (SEQ ID NO:26) TCCTGCGGCCTAGCTCTGA; 3' IFN-γ primer, (SEQ ID NO:27) GCCATGAGGAAGAGCT; IFN-γ probe, (SEQ ID NO:28) ACAATGAACGCTACACACTGCATCTTGGC; 5' IL-10 primer, (SEQ ID NO:29) TGCAGCAGCTCAGAGGGTTC; 3' IL-10 primer, (SEQ ID NO:30) CTGGCCACAGTTTTCAGGGA; IL-10 probe, (SEQ ID NO:31) CCTACTGTCATCCCCAGCCGCTTC; 5' TGF-β primer, (SEQ ID NO:32) GCAACATGTGGAACTCTACCAGAA; 3' TGF-β primer, (SEQ ID NO:33) GACGTCAAAAGACAGCCACTC; TGF-β probe, (SEQ ID NO:34) ACCTTGGTAACCGGCTGCTGACCC. All reactions were performed using the TaqMan Gold PT-PCR kit according to the manufacturer's instructions (PE Applied Biosystems). For the different runs cDNA corresponding to 5 ng of total RNA was used. A normalization to ribosomal RNA was performed for each sample.

Statistical analysis. Disease was compared using an Analysis of Maximum Likelihood Estimate and incidence rate. Proliferation measurements were compared using an F-ratio and student's t-test.

Results

NOD mice immunized with plasmid encoding the insulin B chain peptide 9-23 are protected from diabetes. To test the efficacy of an insulin DNA vaccine in the NOD mouse model, groups of 10, 4-week-old NOD mice were injected with the DNA vaccine constructs and monitored for diabetes weekly, as determined by glucosuria and hyperglycemia, for >30 weeks. Results represent two independent experiments. Animals were monitored for glucosuria twice weekly. Diabetes was established by two consecutive readings >250 mg/dl, and confirmed by blood glucose measurement. Data shown represents 10+10 mice studied over two experiments.

Figure 5:
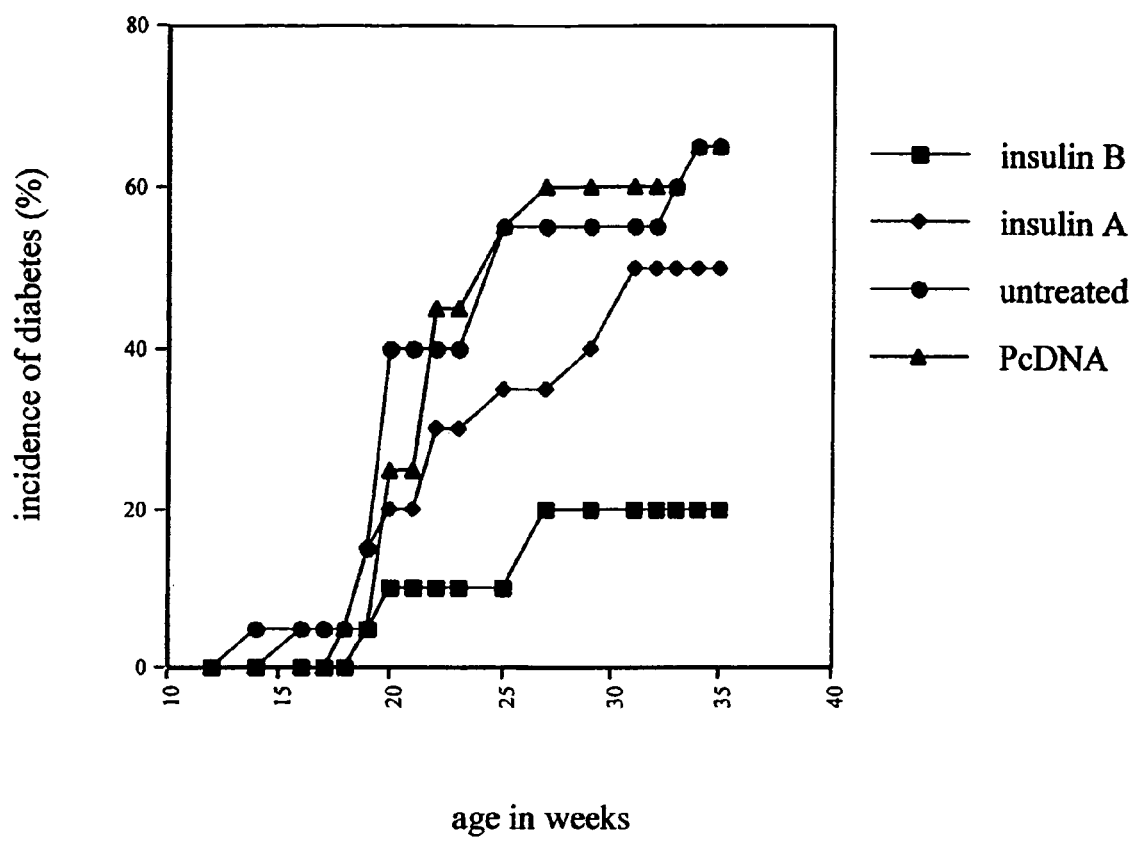
FIG. 5. Incidence of diabetes in DNA vaccinated NOD mice. Female NOD mice were injected with either empty plasmid DNA (▲), plasmid encoding insulin B (9-23) (■), or plasmid encoding insulin A (7-21) (♦); one group was left untreated (●).

In the untreated and plasmid control (PcDNA) injected groups, 70% of the mice developed diabetes by 34 weeks of age (FIG. 5). In the insB-PcDNA injected group, however, only 20% developed diabetes by the same age (p=0.02 by $X^2$ analysis). Furthermore, the onset of disease was markedly delayed in this group as well, from <14 weeks for the first animal to become diabetic in the untreated group, to >17 weeks for the insB-PcDNA vaccinated group. The diabetes incidence rate for the PcDNA and untreated control groups was 3 times the rate for the insB-PcDNA group (0.035 and 0.036 for the PcDNA and untreated groups, respectively, compared to 0.012 for insB-PcDNA group.)

In InsB-PcDNA vaccinated NOD mice, insulitis coexists with protection. Pancreata were removed from immunized and control animals at 7 weeks of age, a time at which the initial infiltration of some islets is clearly visible by histological staining of NOD pancreata. A minimum of twenty-five islets each for five animals per group were scored for insulitis. Staining of pancreata from older (16-week-old) mice yielded similar results. Although animals injected with insulin DNA showed no clinical signs of diabetes, islet infiltration (insulitis) was visible at levels comparable to that seen in the control animals. Hence vaccination with insulin DNA did not affect gross trafficking of lymphocytes to the islets of Langerhans.

Proliferative responses of InsB-PcDNA Vaccinated NOD splenocytes against insulin are unaltered compared to controls. Spleens were harvested from immunized animals 10 days following the third immunization and tested for proliferative responses against insulin. We found a modest but not significant increase in proliferation by InsB-PcDNA immunized splenocytes compared to controls, which may reflect priming of the small population of insulin-specific cells. Nonetheless, these results indicate that the mechanism of protection from IDDM is not dependent on induction of anergy in insulin-specific cells.

Insulin-specific antibodies are not induced by InsB-PcDNA vaccination. We tested whether DNA immunization induced antibodies against the insulin peptide, or against other NOD autoantigens. Mice were bled at early (8 weeks) and late (25 weeks) time points, and the serum tested by ELISA for antibodies against whole insulin, insulin B (9-23), insulin A (7-21), GAD65, and Hsp60. We found no differences between groups in antibody levels against the insulin B peptide, nor against any of the other candidate antigens.

Immunization with Insulin B (9-23) DNA induces an antigen-specific response in the pancreatic lymph nodes. In order to detect antigen-specific responses in vitro, we used quantitative PCR to assess levels of cytokine mRNA production (FIG. 6). Pancreatic lymph node cells from NOD mice vaccinated twice at a ten day interval with either PcDNA or InsB-PcDNA were harvested 5 days after the second injection. Cells were cultured in the presence of insulin B (9-23) peptide for 72 hours, then pelleted for quantitative PCR analysis of cytokine mRNA levels.

In three independent experiments, groups of animals were injected twice with either the insB-PcDNA or the PcDNA control plasmid. Five days after the second injection, pancreatic lymph nodes were harvested and single-cell suspension plated with 10 μg/mL insulin B (9-23) peptide. After 72 hours the cells were pelleted, and subjected to quantitative PCR analysis for IL-4, TGF-β, IL-10, and IFN-γ message levels. Quantitative PCR comparison of cytokine message levels in pancreatic lymph node cells showed a significant reduction in IFN-γ and IL-10 levels in the insB-PcDNA vaccinated animals compared to PcDNA—vaccinated controls. IFN-γ levels from insB-PcDNA-vaccinated lymph nodes were 38% that of PcDNA vaccinated lymph nodes (p<0.05) in response to insulin B peptide stimulation. Furthermore, IL-10 levels in InsB-PcDNA vaccinated mice were 30% of PcDNA control levels (p<0.01). Changes in mRNA levels of IL-4 and TGF-β were not significant over the three experiments.

The above data demonstrate the successful vaccination of NOD mice with insulin B (9-23) DNA to confer protection from diabetes. The effect is specific to DNA encoding immunogenic insulin, since empty plasmid alone, or DNA encoding a non-immunogenic peptide of insulin, did not have a significant effect on disease. Bacterial CpG motifs could not account for the protection, since the plasmid encoding insulin A (7-21), which was identical in length and contained the same number of CpGs, did not alter disease incidence significantly. Disease onset was substantially delayed in the InsB-PcDNA vaccinated mice that did become diabetic, reiterating the protective potential of DNA vaccination. Protection from diabetes appeared to be associated with down regulation of IFN-γ and IL-10 in pancreatic lymph node cells in response to the insulin B peptide encoded in the vaccine.

Insulitis was not abolished in protected animals, indicating that DNA vaccination did not reduce the gross trafficking of cells to the islets, although there may be a selective alteration in lymphocyte trafficking. Furthermore, the infiltrate was relatively non-destructive within the time of analysis (up to 16 weeks of age), as most InsB-PcDNA vaccinated mice did not become diabetic. This outcome is consistent with data describing polypeptide based immunization with whole insulin or with the B chain peptide. Regulation of diabetes does not necessarily take place at the level of infiltration of the islets by lymphocytes, but rather, at the level of the actual destruction of the insulin-secreting β cells.

There was no significant increase in T cell proliferative responses to insulin B peptide and whole insulin by splenocytes of insB-PcDNA vaccinated animals. This result indicates that insulin B (9-23) DNA vaccination in the NOD mice does not anergize or eliminate T cells specific for the encoded peptide. Rather, it was found that cells from insB-PcDNA immunized animals expressed substantially lower amounts of IFN-γ than did cells from control vaccinated animals. This down regulation of IFN-γ secretion in response to activation correlates strongly with protection from diabetes, since IFN-γ is known to be a critical mediator of inflammation of the islets and of β cell destruction. The decrease in levels of IL-10 expression may also contribute to protection from disease.

These results suggest that DNA vaccination may be an effective method of altering harmful immune responses in autoimmunity to confer protection. Furthermore, DNA vaccination will be a powerful tool in modulating disease.

---

What is claimed is:

1. A method of reducing destruction of β cells in a mammal in need thereof, the method comprising administering intramuscularly to the mammal a modified plasmid DNA vector comprising an expression cassette, the expression cassette comprising a promoter active in mammalian cells operably linked to a DNA encoding an insulin autoantigen targeted in IDDM, wherein the insulin autoantigen is selected from the group consisting of insulin B chain, pre-proinsulin, and pro-insulin, wherein the modified plasmid DNA vector has a low number of CpG motifs compared to an unmodified plasmid DNA vector, so as to thereby reduce the destruction of β cells in the mammal.

2. The method of claim 1, wherein the autoantigen is a polypeptide.

3. The method of claim 1, wherein the autoantigen is a peptide.

4. The method of claim 1, wherein the autoantigen is insulin B chain.

5. The method of claim 1, wherein the autoantigen is proinsulin.

6. The method of claim 1, wherein the autoantigen is pre-proinsulin.

7. The method of claim 1, wherein the mammal is a human.

8. The method of claim 1, wherein the plasmid DNA vector is administered during the presymptomatic stage of IDDM.

9. The method of claim 8, wherein the presymptomatic stage of IDDM is indicated by a marker selected from the group consisting of increased T lymphocytes in the pancreas, increased islet cell antibodies, reduced plasma insulin C-peptide and decreased plasma insulin concentration.

10. The method of claim 1, wherein the β cell function is evidenced by plasma levels of insulin C-peptide.

* * * * *

UNITED STATES PATENT AND TRADEMARK OFFICE
CERTIFICATE OF CORRECTION

PATENT NO. : 7,579,328 B2  
APPLICATION NO. : 11/289226  
DATED : August 25, 2009  
INVENTOR(S) : Lawrence Steinman et al.

Page 1 of 1

It is certified that error appears in the above-identified patent and that said Letters Patent is hereby corrected as shown below:

At column 1, line 19 please correct as follows:

--This invention was made with Government support under ~~contract NS18235~~ contracts NS018235 and AI079320 awarded by the National Institutes of Health. The Government has certain rights in this invention.--

Signed and Sealed this  
Eighth Day of March, 2011

David J. Kappos  
*Director of the United States Patent and Trademark Office*